(12) United States Patent
Sutti et al.

(10) Patent No.: US 11,337,845 B2
(45) Date of Patent: May 24, 2022

(54) DYNAMIC CUSHION HEEL-ANKLE-FOOT ORTHOSIS

(71) Applicant: Kinematic Improvements LLC, Plano, TX (US)

(72) Inventors: Nathan Joseph Sutti, Plano, TX (US); Franck Vautrin, Dallas, TX (US); Jeff Robbins, Aubrey, TX (US)

( * ) Notice: Subject to any disclaimer, the term of this patent is extended or adjusted under 35 U.S.C. 154(b) by 652 days.

(21) Appl. No.: 16/100,846

(22) Filed: Aug. 10, 2018

(65) Prior Publication Data

US 2018/0344502 A1  Dec. 6, 2018

Related U.S. Application Data

(63) Continuation-in-part of application No. 15/714,817, filed on Sep. 25, 2017, now abandoned, which is a continuation-in-part of application No. 15/133,167, filed on Apr. 19, 2016, now Pat. No. 10,123,897, which is a continuation-in-part of application No. 14/859,107, filed on Sep. 18, 2015, now Pat. No. 10,278,853.

(60) Provisional application No. 62/138,535, filed on Mar. 26, 2015.

(51) Int. Cl.
*A61F 5/00* (2006.01)
*A61F 5/01* (2006.01)
*A61H 3/00* (2006.01)

(52) U.S. Cl.
CPC .......... *A61F 5/0127* (2013.01); *A61F 5/0111* (2013.01); *A61H 3/00* (2013.01); *A61H 2205/125* (2013.01)

(58) Field of Classification Search
None
See application file for complete search history.

(56) References Cited

U.S. PATENT DOCUMENTS

| | | | |
|---|---|---|---|
| 6,868,586 B1 * | 3/2005 | Hall | A63B 21/0552 24/115 A |
| 7,458,135 B2 * | 12/2008 | Mikesell | B25H 3/006 24/300 |
| 9,585,770 B2 * | 3/2017 | Simmons, III | A43B 3/0015 |
| 2010/0324463 A1 * | 12/2010 | Klotz | A61F 5/0113 602/28 |

(Continued)

FOREIGN PATENT DOCUMENTS

WO   WO-02065942 A2 *   8/2002   ............ A61F 5/0111

*Primary Examiner* — Kim M Lewis
(74) *Attorney, Agent, or Firm* — Miller IP Law LLC

(57) ABSTRACT

A method, system, apparatus, and/or device for supporting a plantar flexion ridge. The method, system, apparatus, and/or device may include a leg calf shell further with a leg calf shell plantar flexion ridge at a lowermost point. The method, system, apparatus, and/or device may include a boot shell connected to a bottom portion of the leg calf shell. The boot shell may include a boot shell plantar flexion ridge at an uppermost point or the boot shell. The boot shell plantar flexion ridge may contact the leg calf shell plantar flexion ridge at a plantar flexion ridges region. The method, system, apparatus, and/or device may include a posterior stretch cord assembly. The first end of the posterior stretch cord assembly may attach to a back of the leg calf shell and the second end of the posterior stretch cord assembly may be attached to a back of the boot shell.

6 Claims, 19 Drawing Sheets

(56) References Cited

U.S. PATENT DOCUMENTS

| | | | |
|---|---|---|---|
| 2012/0029401 A1* | 2/2012 | Caldwell | A61F 5/0113 602/16 |
| 2014/0066829 A1* | 3/2014 | Drillio | A61F 5/0127 602/27 |
| 2015/0045709 A1* | 2/2015 | Wiley | A61F 5/0111 602/28 |
| 2016/0067075 A1* | 3/2016 | Malinowski | A61F 5/0113 602/28 |
| 2016/0135978 A1* | 5/2016 | McGovern | A61F 5/0127 602/27 |

* cited by examiner

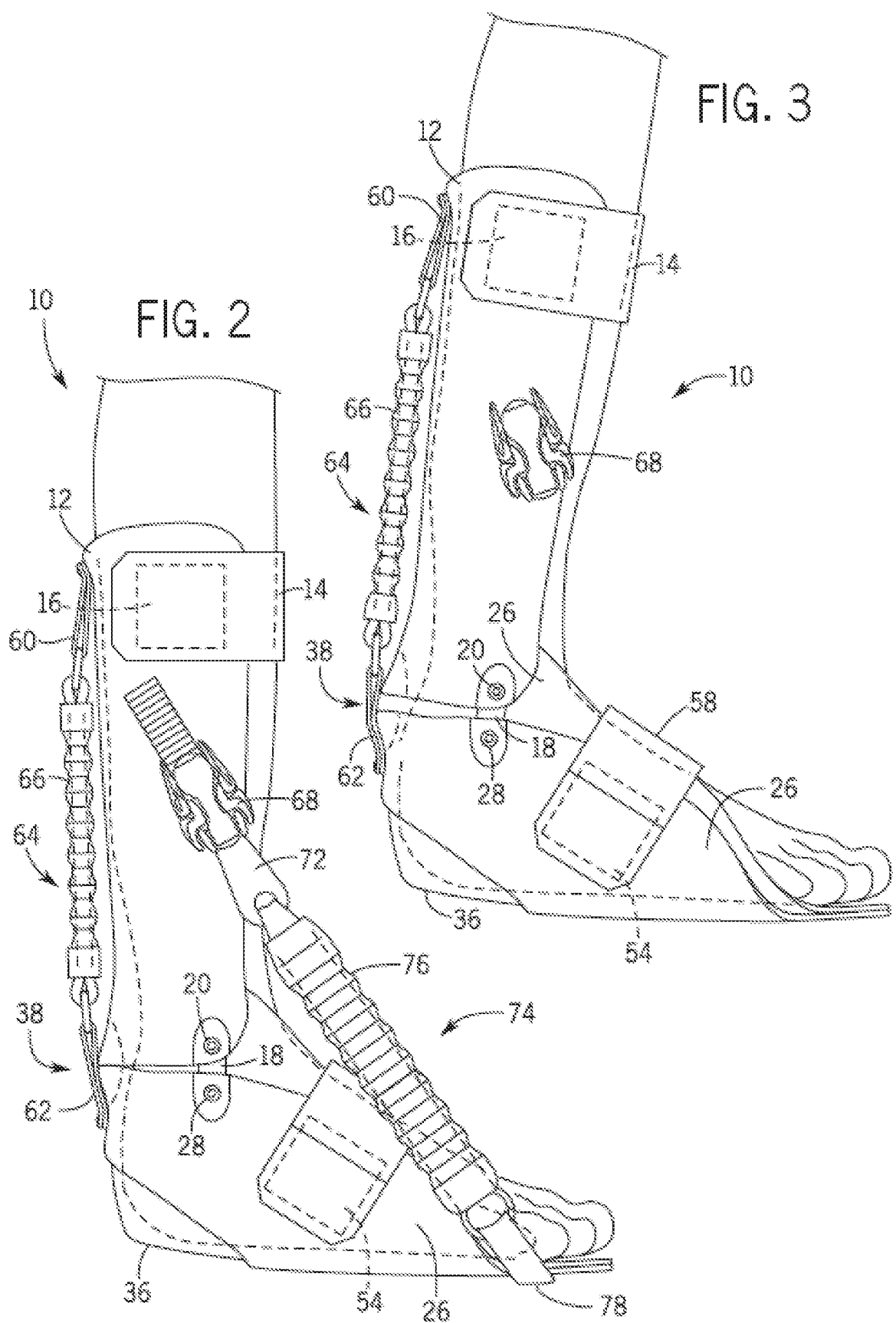

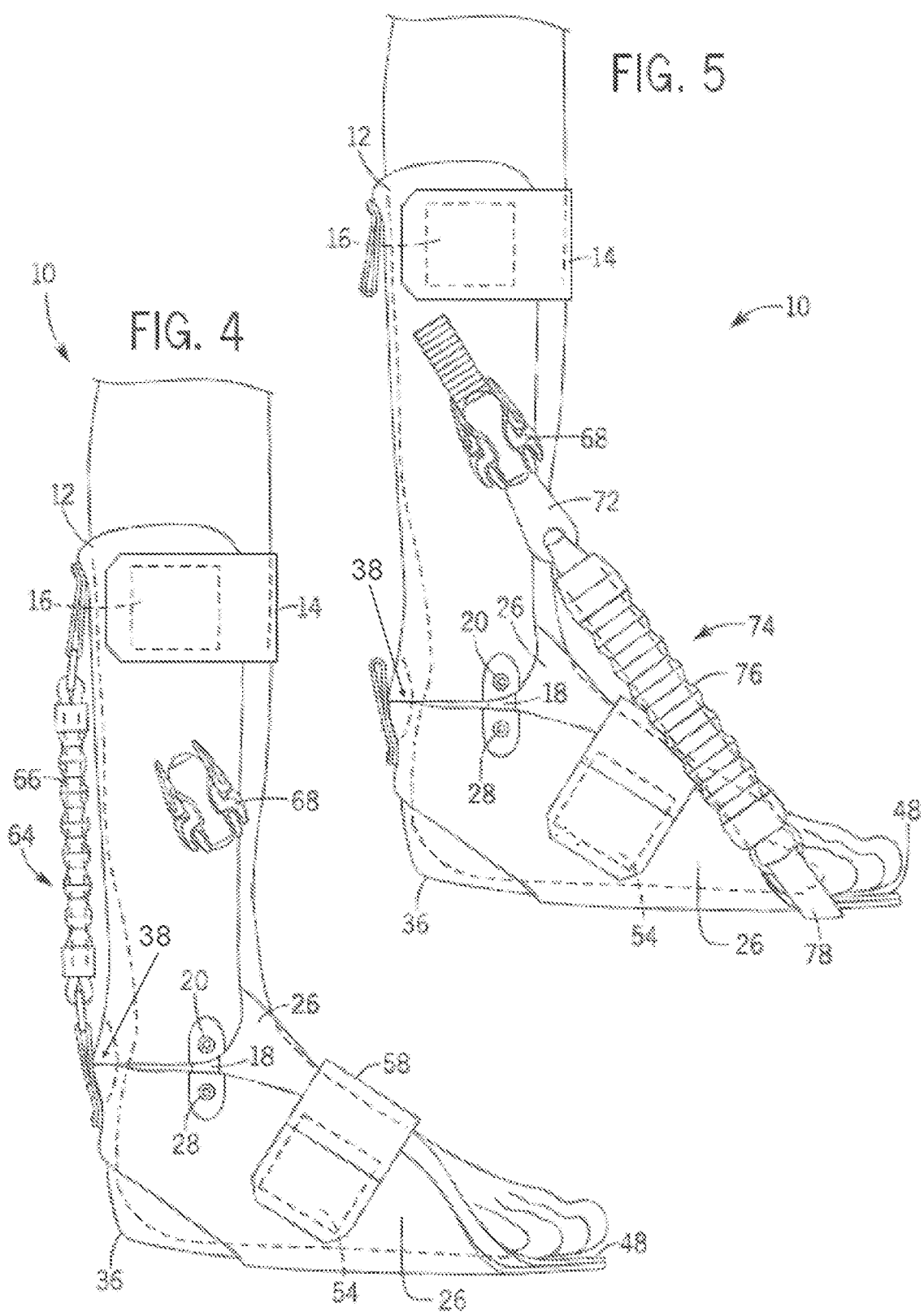

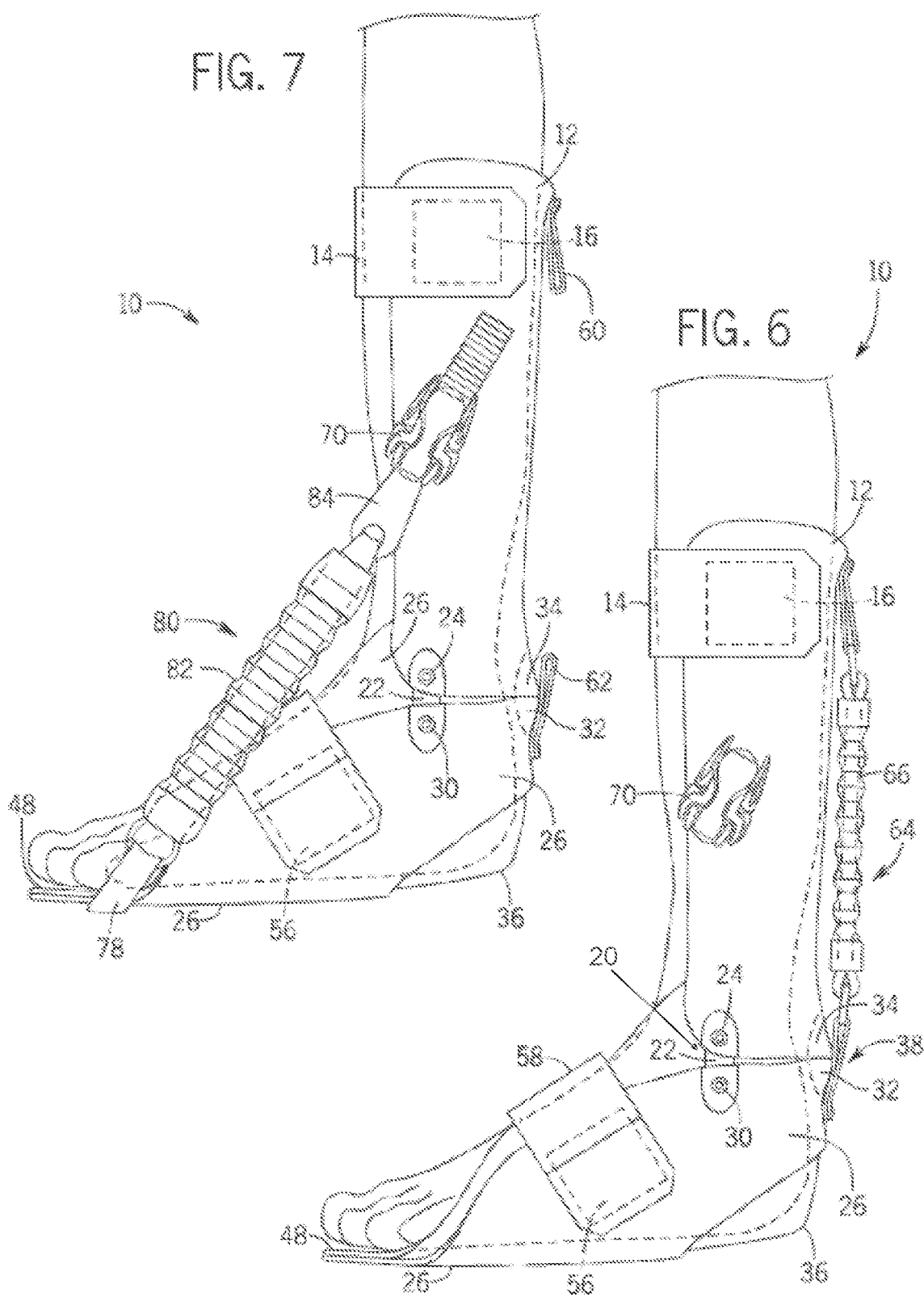

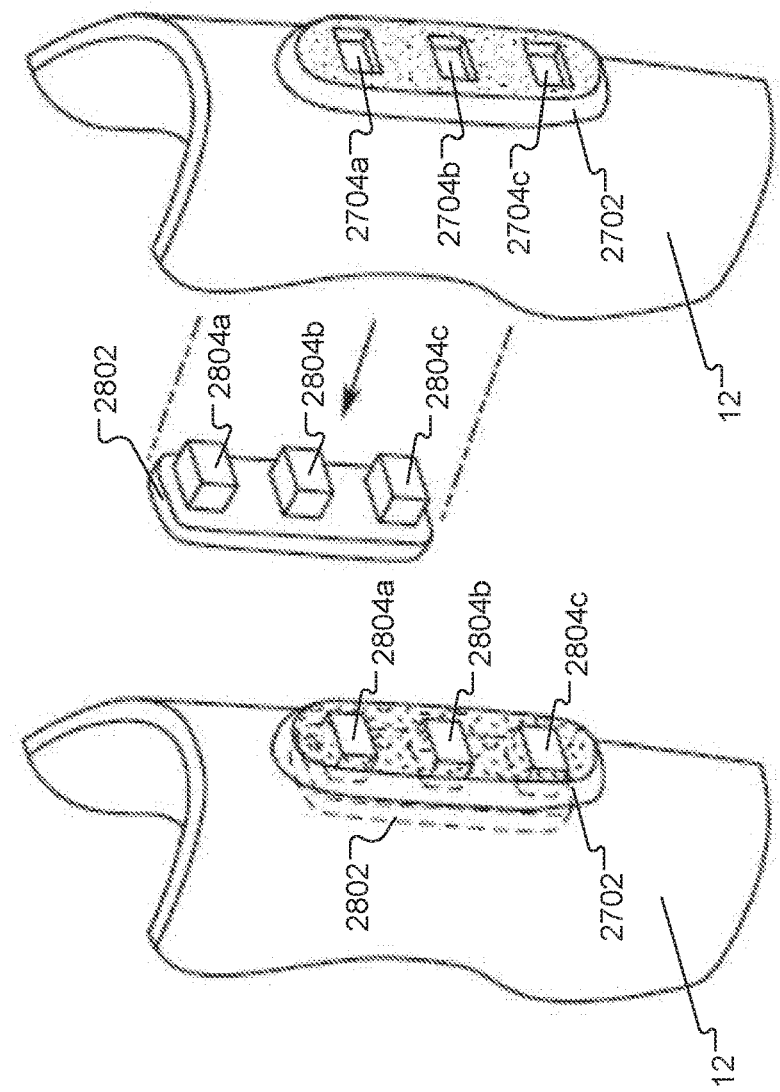
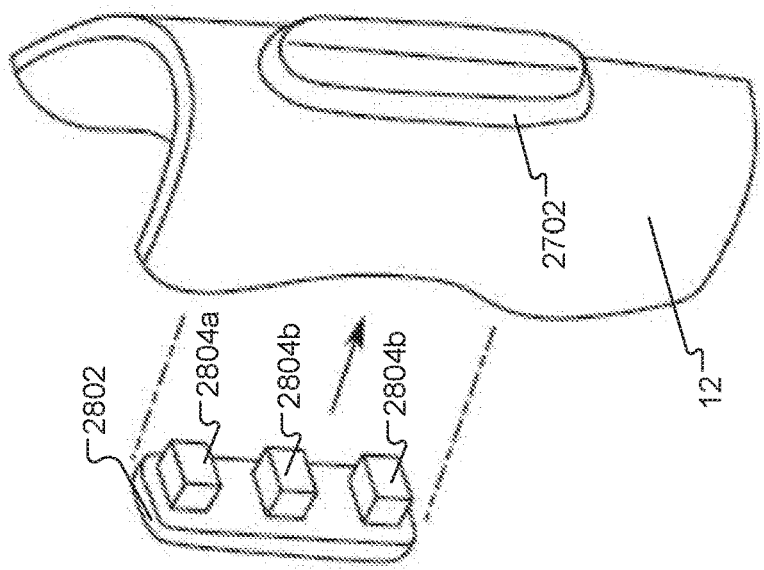

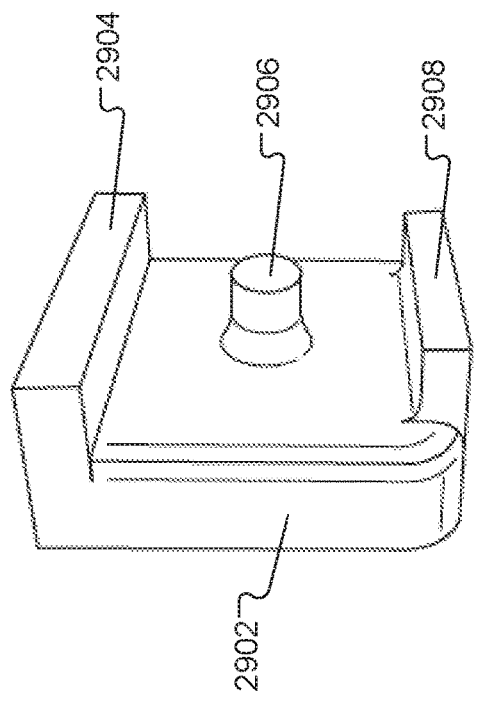
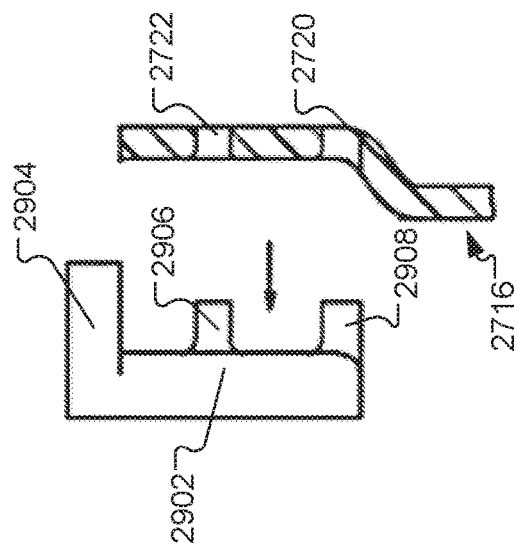
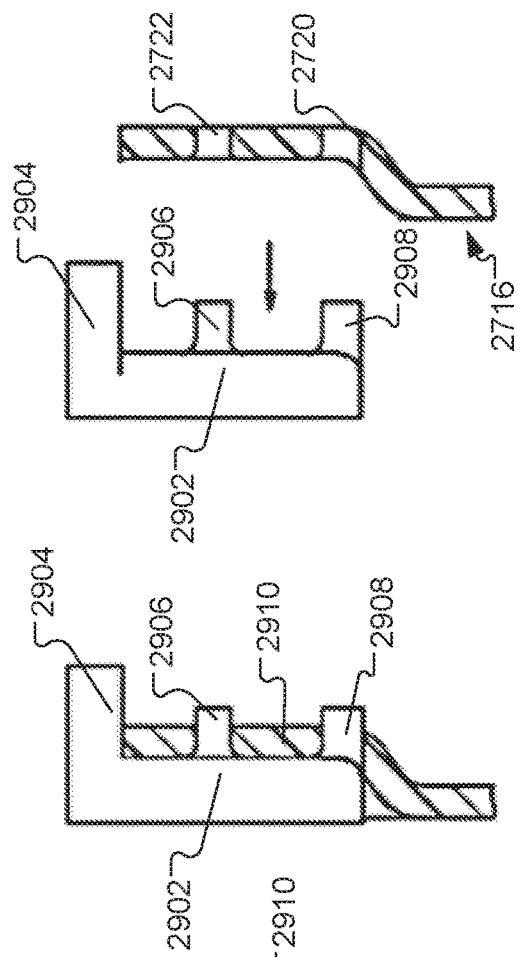
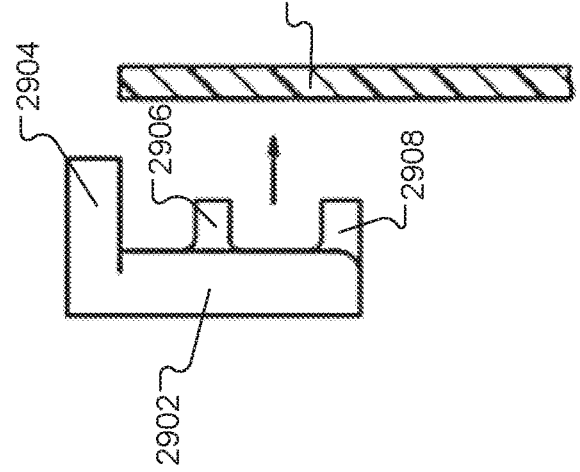

DYNAMIC CUSHION HEEL-ANKLE-FOOT ORTHOSIS

CROSS REFERENCE TO RELATED APPLICATIONS

This application is a continuation-in-part of U.S non-provisional application Ser. No. 15/714,817, filed Sep. 25, 2017, which is a continuation-in-part of non-provisional patent application U.S. Ser. No. 15/133,167 filed on Apr. 19, 2016. The non-provisional patent application U.S. Ser. No. 15/133,167 is a continuation-in-part of non-provisional patent application U.S. Ser. No. 14/859,107 filed on Sep. 18, 2015, which, in turn, claims priority to provisional patent application U.S. Ser. No. 62/138,535 filed on Mar. 26, 2015. The entire contents of all applications are herein incorporated by reference.

BACKGROUND

An orthosis is a device used to modify the structural and functional characteristics of the neuromuscular and skeletal system. An orthosis may be used for the correction of disorders of the limbs or spine correct alignment and/or provide support. For example, orthosis may be used to correct alignment and/or provide support to the heel, ankle, and foot of an individual. Examples of simple orthosis devices may include casts, splints, and braces.

BRIEF DESCRIPTION OF THE DRAWINGS

The detailed description of some embodiments of the invention is made below with reference to the accompanying FIGs, wherein like numerals represent corresponding parts of the figures.

FIG. 2 illustrates a side elevation view perspective view of the dynamic cushion heel-ankle-foot orthosis, according to an embodiment.

FIG. 3 illustrates a side elevation view perspective view of the dynamic cushion heel-ankle-foot orthosis, according to an embodiment.

FIG. 4 illustrates a side elevation view of the dynamic cushion heel-ankle-foot orthosis, according to an embodiment.

FIG. 5 illustrates another side elevation view of the dynamic cushion heel-ankle-foot orthosis, according to an embodiment.

FIG. 6 illustrates another side elevation view of the dynamic cushion heel-ankle-foot orthosis as illustrated in FIGS. 1A-1D, according to an embodiment.

FIG. 7 illustrates another side elevation view of the dynamic cushion heel-ankle-foot orthosis as illustrated in FIGS. 1A-1D, according to an embodiment.

FIG. 28A illustrates a process step of forming the buckle attachment into the leg calf shell, according to an embodiment.

FIG. 28B illustrates a process step of pressing the fastener form into the leg calf shell to form the buckle attachment, according to an embodiment.

FIG. 28C illustrates a process step of removing the fastener form from the leg calf shell to form the buckle attachment, according to an embodiment.

FIG. 29A illustrates a process step of forming the locking portion, according to an embodiment.

FIG. 29B illustrates a process step of forming the locking form, according to an embodiment.

FIG. 29C illustrates a process step of pressing the locking form into formable material to form the locking portion, according to an embodiment.

FIG. 29D illustrates a process step of removing the locking form from the formable material to form the locking portion, according to an embodiment

DETAILED DESCRIPTION

Figure 1A:
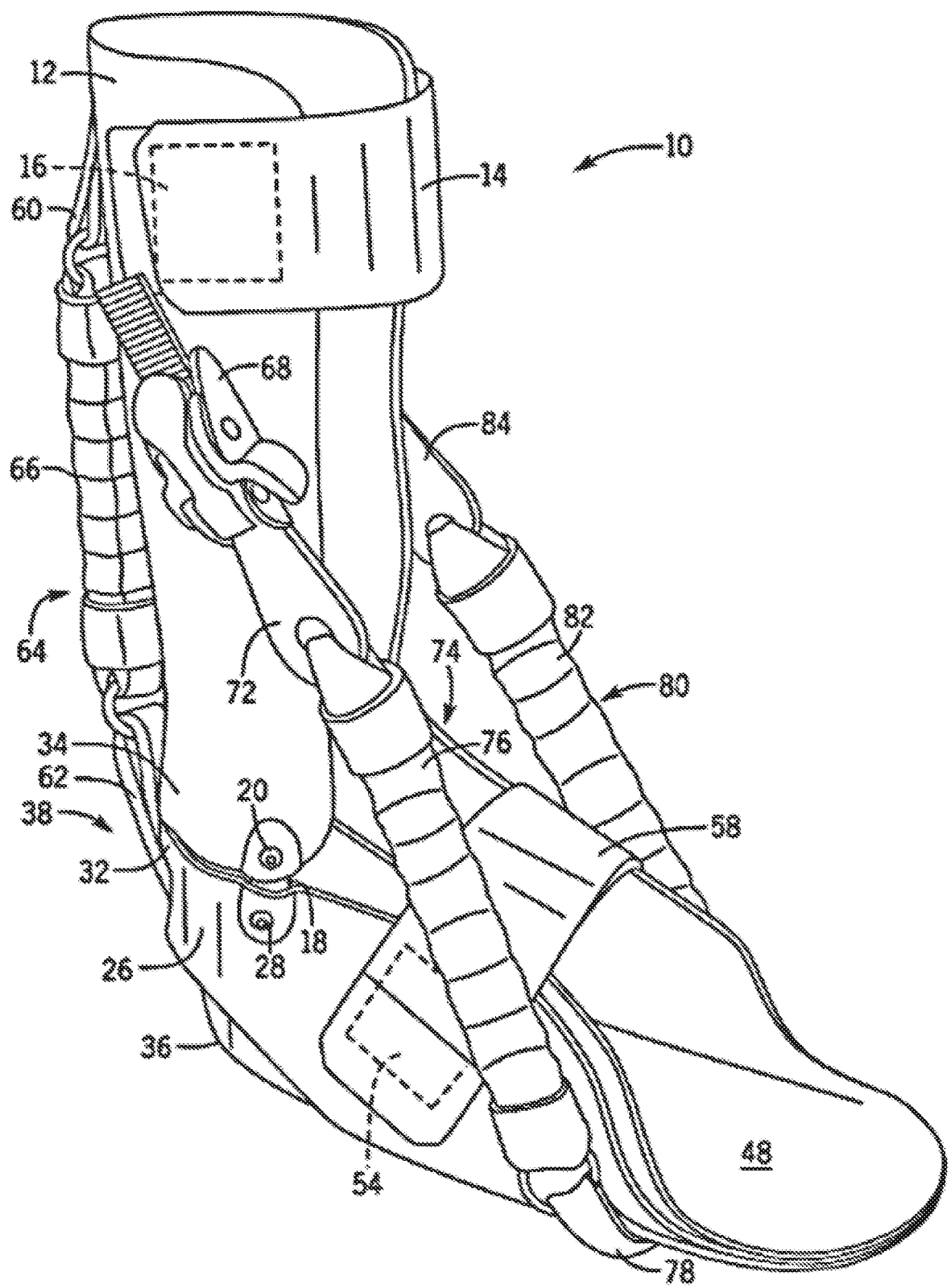
FIG. 1A illustrates a dynamic cushion heel-ankle-foot orthosis comprises leg calf shell attached to leg strap with hook and loop fastener.

The disclosed dynamic cushion heel-ankle-foot orthoses will become better understood through review of the following detailed description in conjunction with the figures. The detailed description and FIGs provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of dynamic cushion heel-ankle-foot orthosis examples are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

An orthosis may at least immobilize a limb of an individual and protect the limb from further injury. A patient that uses of an orthosis often present with sagittal instabilities which require the use of a plantar flexion stop built into the device. The patient may also have difficulty controlling tibial progression and lack the ability to produce plantarflexion push off in late stance for propulsion and utilization of their third rocker. The patient may also have limited range of motion.

When a plantar flexion stop is used within a conventional orthosis, the plantar flexion stop may create an abrupt knee flexion moment at the initial part of gait which is not part of normal kinematics. Additionally, the plantar flexion stop may be used in cases such as plantar flexion contractures or knee hyperextension. However, conventional orthosis devices may not provide controlled tibial progression, decrease plantarflexion moment at initial contact, and decrease contractures. Furthermore, conventional orthosis devices may not produce an active plantar flexion moment in late stance and stretch contracted muscles, which may be used for both ambulation and therapeutic applications.

Implementations of the disclosure address the above-mentioned deficiencies and other deficiencies by providing a method, system, device, and/or apparatus provide controlled tibial progression, decrease plantarflexion moment at initial contact, decrease contractures, produce active plantar flexion moments in late stance, and stretch contracted muscles. The method, system, device, or apparatus may utilize an orthotic device with an anterior and posterior cord assembly. In one embodiment, a dynamic cushion heel-ankle-foot orthosis system may be configured to provide controlled tibial progression and active plantarflexion in a patient. The dynamic cushion heel-ankle-foot orthosis system may include a leg calf shell that includes a leg calf shell plantar flexion ridge at a lowermost point. A boot shell may be rotatably connected to the leg calf shell and include a boot shell plantar flexion ridge at an uppermost point. The boot shell plantar flexion ridge may contact the leg calf shell plantar flexion ridge at a plantar flexion ridges region and rotate no further.

In one embodiment, a heel portion may be joined to the boot shell, where the heel portion includes an outer layer fused to an inner layer. A cushion layer may be between the outer layer and the inner layer. A carbon footplate may be fused to a portion of the outer layer. In another embodiment, a first fastener portion and a second fastener portion may be attached to the boot shell. An upper may be attached to the first fastener portion and the second fastener portion.

In another embodiment, an upper connection loop may be attached to a back portion of the leg calf shell. A lower connection loop may be attached to the boot shell. A posterior stretch cord assembly may be connected to the upper connection loop and the lower connection loop. In another embodiment, the posterior stretch cord assembly may include a hollow cord partially filled with a first retainer end and a second retainer end. A posterior stretch cord sheath may be slid over the hollow cord. A first ring and a second ring may be connected to the posterior stretch cord sheath. A first clip and a second clip may be wrapped around the posterior stretch cord sheath. A first rubber sleeve may be covering the first clip. A second rubber sleeve may be covering the second clip.

In another embodiment, a first buckle and a second buckle may be attached to the leg calf shell. A first connector strap may be adjustably connected to the first buckle. A first anterior stretch cord assembly may be attached to the first connector strap. A first anterior stretch cord sheath may be covering the first anterior stretch cord assembly. A flat stretch cord may be attached to the first anterior stretch cord assembly. A second anterior stretch cord assembly may be attached to the flat stretch cord. A second anterior stretch cord sheath may be covering the second anterior stretch cord assembly. A second connector strap may be attached to the second anterior stretch cord assembly and the second buckle.

FIG. 1A illustrates a dynamic cushion heel-ankle-foot orthosis 10 comprises a leg calf shell 12 attached to a leg strap 16 with a hook and a loop fastener, according to an embodiment. The leg calf shell 12 may be attached to the first connecting member 18 with the first connecting member first fastener 20. The leg calf shell 12 is further attached to the second connecting member 22 with the second connecting member first fastener 24. The first connecting member 18 is further attached to the boot shell 26 with the first connecting member second fastener 28. The second connecting member 22 is further attached to the boot shell 26 with the second connecting member second fastener 30.

The upper portion of the boot shell 26 may be a boot shell plantar flexion ridge 32. The lower portion of the leg calf shell 12 may be a leg calf shell plantar flexion ridge 34. When the leg calf shell 12 is rotated toward the heel portion 36, the boot shell plantar flexion ridge 32 may contact the leg calf shell plantar flexion ridge 34 at a plantar flexion ridges region 38 and rotate no further in that direction. In one embodiment, the leg calf shell 12 may rotate counterclockwise toward the heel portion 36 and the boot shell plantar flexion ridge 32. In another embodiment, the leg calf shell 12 may rotate clockwise toward the heel portion 36 and the boot shell plantar flexion ridge 32.

The boot shell 26 may be attached to the first fastener portion 54 and the second fastener portion 56. The first fastener portion 54 and the second fastener portion 56 are attached to the upper portion 58. In one embodiment, the first fastener portion 54 and the second fastener portion 56 may be hook fasteners and a loop fastener may be attached to the upper portion 58. In another embodiment, the upper portion 58 may be adjustable.

A back portion of leg calf shell 12 may be attached to the upper connection loop 60. The boot shell 26 may be attached to the lower connection loop 62. The upper connection loop 60 may be joined to the lower connection loop 62 with the stretch cord assembly 64 which is covered with the stretch cord sheath 66.

The leg calf shell 12 may be attached to the first buckle 68 and the second buckle 70. The first buckle 68 may be adjustably connected to the first connector 72. The first connector 72 may be attached to the first anterior stretch cord assembly 74 covered with the first anterior stretch cord sheath 76. The first anterior stretch cord assembly 74 may be attached to the cord 78. The cord 78 may be attached to the second anterior stretch cord assembly 80 and covered with the first anterior stretch cord sheath 82. The second anterior stretch cord assembly 80 may be attached to the second connector strap 84. The second connector strap 84 may be connected to the second buckle 70.

Figure 1B:
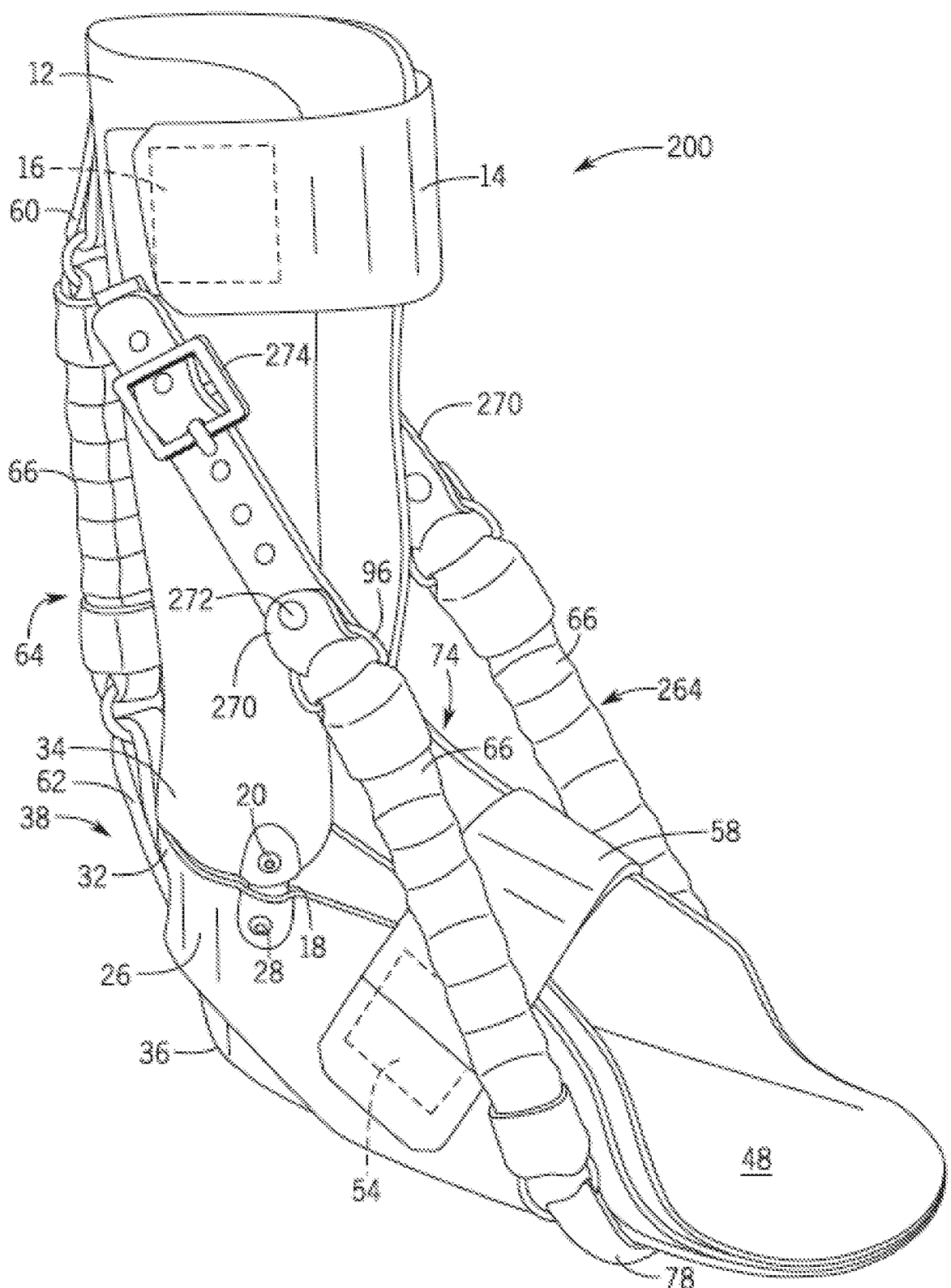
FIG. 1B illustrates a front perspective view of a dynamic cushion heel-ankle-foot orthosis, according to an embodiment.

FIG. 1B illustrates a front perspective view of a dynamic cushion heel-ankle-foot orthosis 200, according to an embodiment. Some of the features in FIG. 1B are the same or similar to some of the features in FIG. 1A as noted by the same reference numbers, unless expressly described otherwise. As discussed above, the back portion of leg calf shell 12 may be attached to the upper connection loop 60 and the boot shell 26 may be attached to the lower connection loop 62. The upper connection loop 60 may be joined to the lower connection loop 62 with the stretch cord assembly 64.

In one embodiment, a front of the leg calf shell 12 may be attached to a front of boot shell 48 by a fastener. The fastener may include a first portion attached to a side of the leg calf shell 12. The first portion may include a connection strap 270 and a connection buckle 274. The connection buckle 274 may be attached to a side of the leg calf shell 12 and the connection strap 270 may extended toward the front of boot shell 48. The second portion of the fastener may include the cord 78 connected to a bottom of the front of boot shell 48 with the stretch cord assembly 64 covered by the stretch cord sheath 66 extending toward an end of the connection strap 270. An end of the stretch cord assembly 64 may include a ring 96. A portion of the connection strap 270 may extend through the first ring 96 and a rivet 272 may then fasten the connection strap 270 to itself and form a loop that secures the connection strap 270 to the stretch cord assembly 64. In one embodiment, the dynamic cushion heel-ankle-foot orthosis 200 may include a single fastener to connect the front of the leg calf shell 12 to the front of boot shell 48. In another embodiment, the dynamic cushion heel-ankle-foot orthosis 200 may include a first fastener to connect the front of the leg calf shell 12 to the front of boot shell 48 at a first side of the dynamic cushion heel-ankle-foot orthosis 200 and a second fastener to connect the front of the leg calf shell 12 to the front of boot shell 48 at a second side of the dynamic cushion heel-ankle-foot orthosis 200.

Figure 1C:
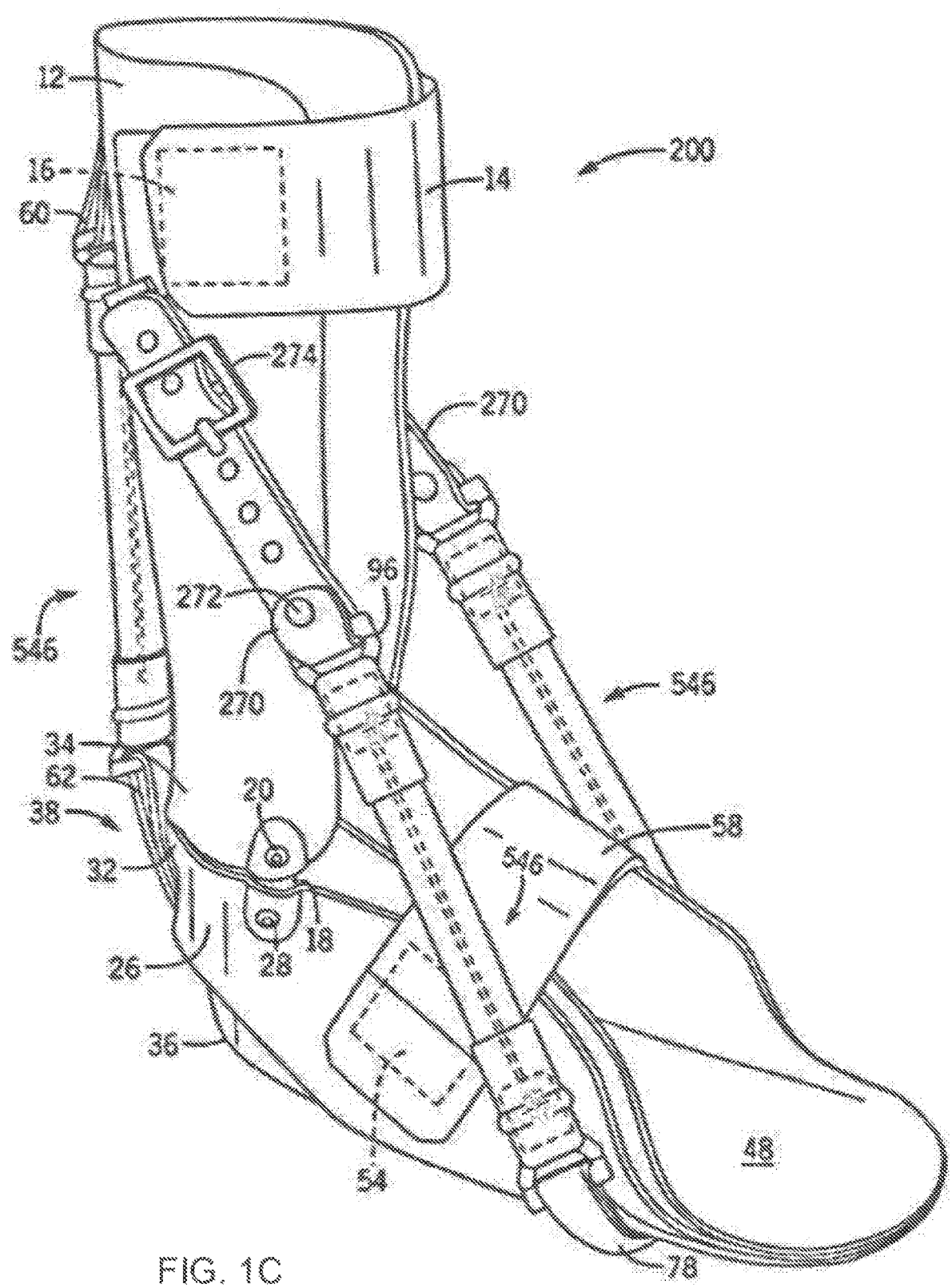
FIG. 1C illustrates a front perspective view of the dynamic cushion heel-ankle-foot orthosis in FIG. 1B with a strap, according to an embodiment.

FIG. 1C illustrates a front perspective view of the dynamic cushion heel-ankle-foot orthosis 200 in FIG. 1B with a stretch cord 546, according to an embodiment. Some of the features in FIG. 1C are the same or similar to some of the features in FIGS. 1A and 1B as noted by the same reference numbers, unless expressly described otherwise. In one embodiment, the back of the leg calf shell 12 may be connected to the back of the front of boot shell 48 by a stretch cord assembly 546. The stretch cord assembly 546 may include a variety of configurations, as illustrated in FIGS. 25A-E.

In one embodiment, a front of the leg calf shell 12 may be attached to a front of boot shell 48 by a fastener. The fastener may include a first portion attached to a side of the leg calf shell 12. The first portion may include the connection strap 270 and the connection buckle 274, as discussed in FIG. 1B. The second portion of the fastener may include the cord 78 connected to a bottom of the front of boot shell 48 with another stretch cord assembly 546 extending toward an end of the connection strap 270. In one embodiment, the cord 78 may be a flat nylon cord connecting the stretch cord assembly 546 to the bottom of the front of boot shell 48. In combination, the connection strap 270, the stretch cord assembly 546, and the cord 78 may connect the side of the leg calf shell 12 to the bottom of the front of boot shell 48. An end of the stretch cord assembly 546 may include the first ring 96. A portion of the connection strap 270 may extend through the first ring 96 and a rivet 272 may then fasten the connection strap 270 to itself and form a loop that secures the connection strap 270 to the stretch cord assembly 546. In one embodiment, the dynamic cushion heel-ankle-foot orthosis 200 may include a single fastener to connect the front of the leg calf shell 12 to the front of boot shell 48. In another embodiment, the dynamic cushion heel-ankle-foot orthosis 200 may include a first fastener to connect the front of the leg calf shell 12 to the front of boot shell 48 at a first side of the dynamic cushion heel-ankle-foot orthosis 200 and a second fastener to connect the front of the leg calf shell 12 to the front of boot shell 48 at a second side of the dynamic cushion heel-ankle-foot orthosis 200.

Figure 1D:
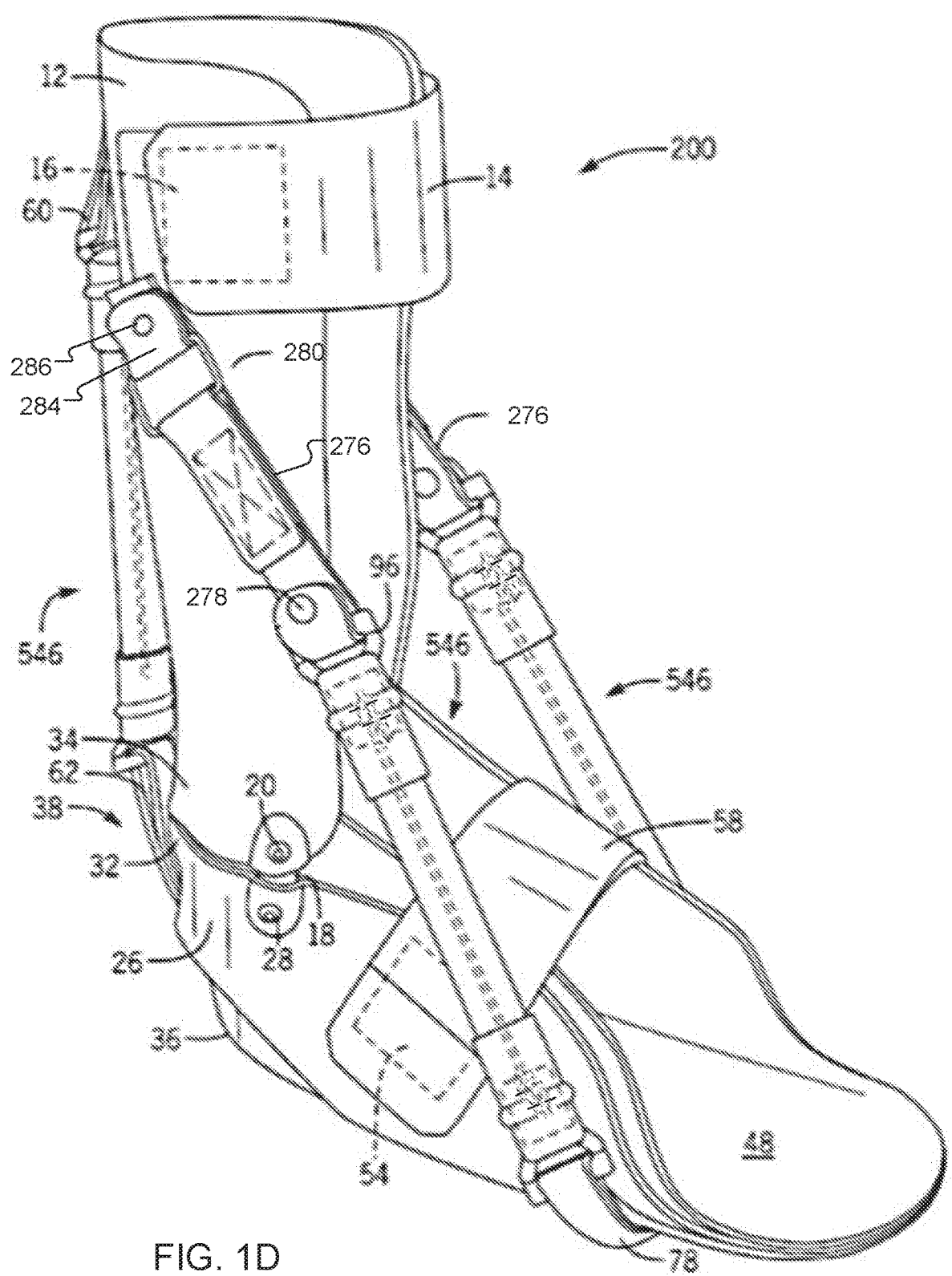
FIG. 1D illustrates a front perspective view of another dynamic cushion heel-ankle-foot orthosis in FIG. 1C with a connector, according to an embodiment.

FIG. 1D illustrates a front perspective view of the dynamic cushion heel-ankle-foot orthosis 200 in FIG. 1C with a first connector 276, according to an embodiment. Some of the features in FIG. 1D are the same or similar to some of the features in FIG. 1A-1C as noted by the same reference numbers, unless expressly described otherwise.

In one embodiment, a front of the leg calf shell 12 may be attached to a front of boot shell 48 by a fastener. The fastener may include a first portion attached to a side of the leg calf shell 12. The first portion may include the first connector 276, a connection ring 280, and an attachment loop 284. The attachment loop 284 may be a piece material that overlaps itself to form a loop that may be fastened to the leg calf shell 12 by a first fastener 286, such as a rivet, a pin, a nail, a screw, and so forth. The connection ring 280 may be located within the loop of the attachment loop 284 and secured within the loop by the first fastener 286. The attachment loop 284 may be connected to a first end of the connector 276. In one embodiment, the connector 276 may include hooks and loops (such as Velcro®) that may fasten around the attachment loop 284. In one example, the first end of the connector 276 may be attached to the connection ring 280 by a portion of the connector 276 that overlaps itself to form a loop that may be fastened around the attachment loop 284 by a second fastener 278, such as a rivet, a pin, a nail, a screw, and so forth. A second end of the connector 278 may be attached to the stretch cord assembly 546, as illustrated and discussed in FIG. 1C. The stretch cord assembly 546 may include a variety of configurations as illustrated in FIGS. 25A-E.

FIG. 2 illustrates a side elevation view perspective view of the dynamic cushion heel-ankle-foot orthosis 10, according to an embodiment. Some of the features in FIG. 2 are the same or similar to some of the features in FIG. 1A-1D as noted by the same reference numbers, unless expressly described otherwise. In one embodiment, when the leg calf shell 12 may rotate counterclockwise toward the heel portion 36, the boot shell plantar flexion ridge 32 may contact the leg calf shell plantar flexion ridge 34 at a plantar flexion ridges region 38 and rotates no further in that direction. In another embodiment, the leg of the user may be in a perpendicular position in the dynamic cushion heel-ankle-foot orthosis 10, where the leg of the user is approximately at a 90-degree angle relative to the foot of the user (as illustrated in FIG. 2).

FIG. 3 illustrates a side elevation view perspective view of the dynamic cushion heel-ankle-foot orthosis 10, according to an embodiment. Some of the features in FIG. 3 are the same or similar to some of the features in FIG. 1A-2 as noted by the same reference numbers, unless expressly described otherwise. In one embodiment, the dynamic cushion heel-ankle-foot orthosis 10 may not include the stretch cord assembly 74 and the connector 72 in FIG. 1A. In another embodiment, the leg of the user may rotate into a forward position in the dynamic cushion heel-ankle-foot orthosis 10, where the leg of the user is at less than a 90-degree angle relative to the foot of the user (as illustrated in FIG. 3).

FIG. 4 illustrates a side elevation view of the dynamic cushion heel-ankle-foot orthosis 10, according to an embodiment. Some of the features in FIG. 4 are the same or similar to some of the features in FIG. 1A-3 as noted by the same reference numbers, unless expressly described otherwise. In one embodiment, the dynamic cushion heel-ankle-foot orthosis 10 may not include the stretch cord assembly 74 and the first connector 72 in FIG. 1A. In another embodiment, the leg of the user may be in a perpendicular position in the dynamic cushion heel-ankle-foot orthosis 10, where the leg of the user is approximately at a 90-degree angle relative to the foot of the user (as illustrated in FIG. 4).

FIG. 5 illustrates another side elevation view of the dynamic cushion heel-ankle-foot orthosis 10, according to an embodiment. Some of the features in FIG. 5 are the same or similar to some of the features in FIG. 1A-4 as noted by the same reference numbers, unless expressly described otherwise. In one embodiment, the dynamic cushion heel-ankle-foot orthosis 10 may not include the stretch cord assembly 64 in FIG. 1A. In another embodiment, the leg of the user may be in a perpendicular position in the dynamic cushion heel-ankle-foot orthosis 10, where the leg of the user is approximately at a 90-degree angle relative to the foot of the user (as illustrated in FIG. 4). The different configuration of the dynamic cushion heel-ankle-foot orthosis 10 and the position of the leg and foot of the user may vary for different applications. In one example, a user may use the dynamic cushion heel-ankle-foot orthosis 10 as illustrated in FIG. 3 or 4 during the day to allow the leg of the user to move between the perpendicular position and the forward position as the user uses his/her leg. In another example, a user may use the dynamic cushion heel-ankle-foot orthosis 10 as illustrated in FIG. 2 or 5 during the night to allow the leg of the user to remain in the perpendicular position as the user sleeps.

FIG. 6 illustrates another side elevation view of the dynamic cushion heel-ankle-foot orthosis as illustrated in FIGS. 1A-1D, according to an embodiment. Some of the features in FIG. 6 are the same or similar to some of the features in FIG. 1A-5 as noted by the same reference numbers, unless expressly described otherwise. In one embodiment, when the leg calf shell 12 is rotated clockwise towards the heel portion 36, the boot shell plantar flexion ridge 32 may contact leg calf shell plantar flexion ridge 34 at a plantar flexion ridges region 38 and rotates no further in that direction.

FIG. 7 illustrates another side elevation view of the dynamic cushion heel-ankle-foot orthosis as illustrated in FIGS. 1A-1D, according to an embodiment. Some of the features in FIG. 7 are the same or similar to some of the features in FIG. 1A-6 as noted by the same reference numbers, unless expressly described otherwise. In one embodiment, the dynamic cushion heel-ankle-foot orthosis 10 may not include the stretch cord assembly 74 and the connector 72. As it rotates clockwise.

Figure 8:
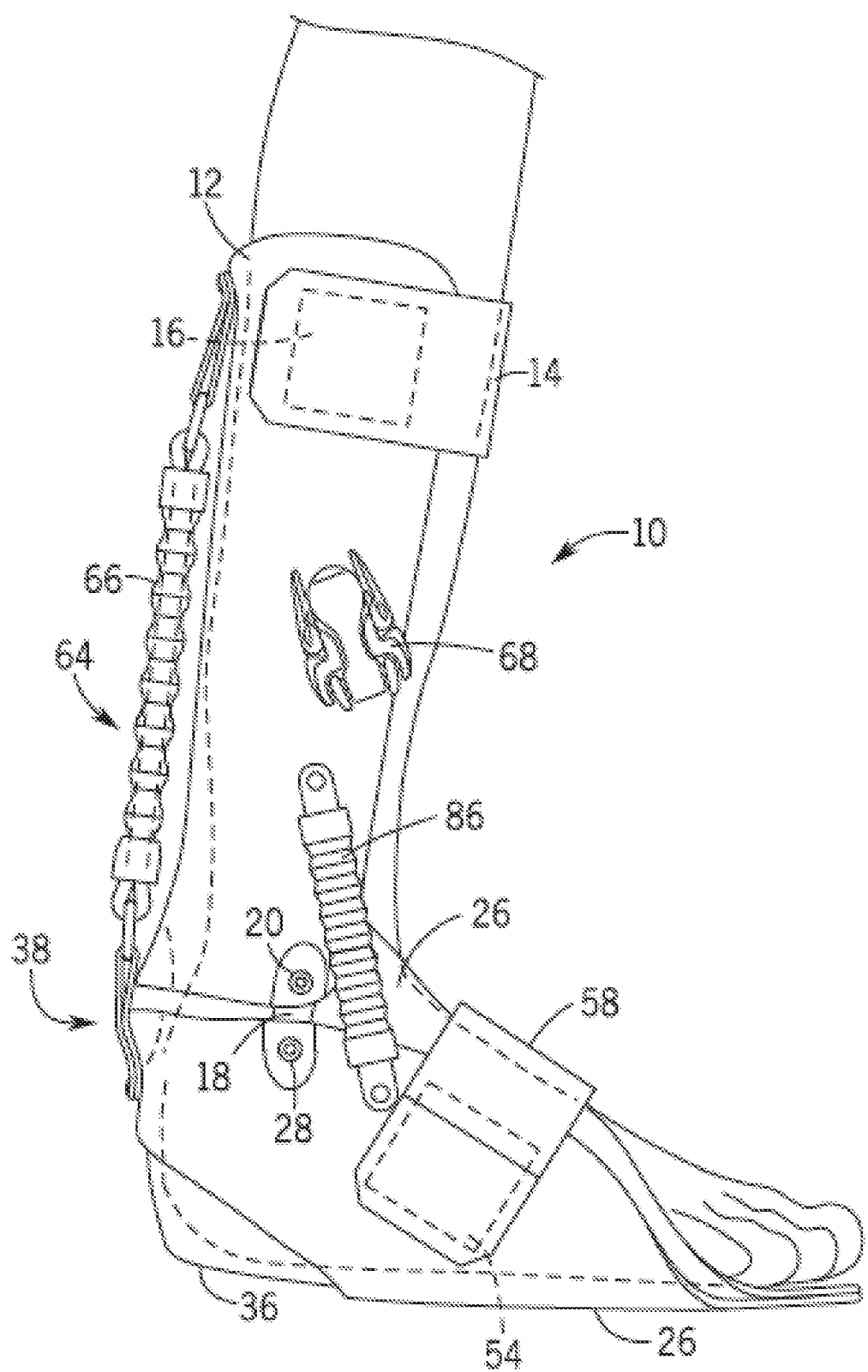
FIG. 8 illustrates another side elevation view of the dynamic cushion heel-ankle-foot orthosis as illustrated in FIGS. 1A-1D, according to an embodiment.

FIG. 8 illustrates another side elevation view of the dynamic cushion heel-ankle-foot orthosis as illustrated in FIGS. 1A-1D, according to an embodiment. Some of the features in FIG. 8 are the same or similar to some of the features in FIG. 1A-7 as noted by the same reference numbers, unless expressly described otherwise. In one embodiment, a direct attachment cord 86 may be used to connect the leg calf shell 12 is rotated clockwise towards the heel portion 36 without regard for buckles or cords.

Figure 9:
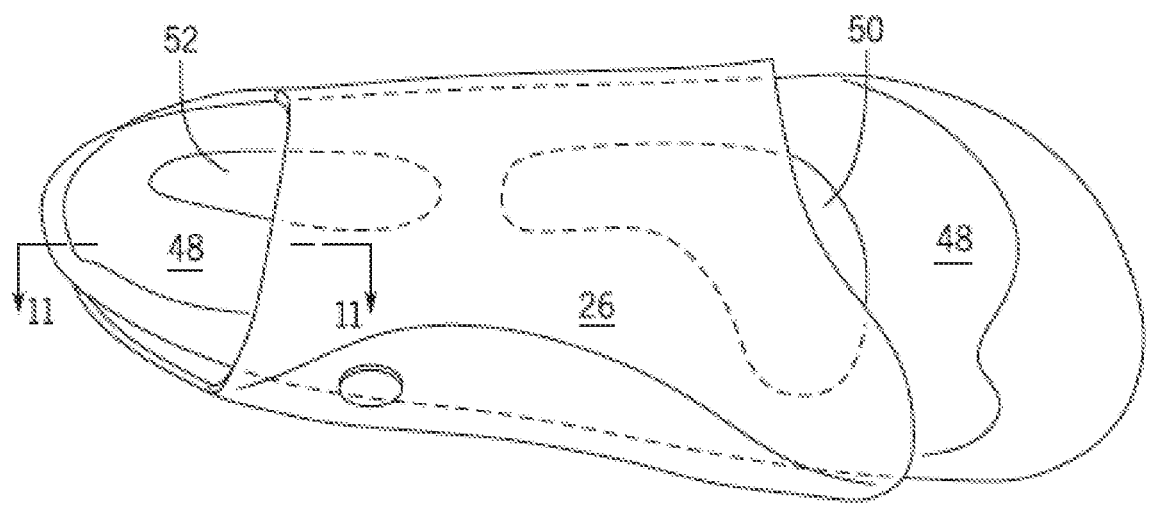
FIG. 9 illustrates a bottom plan view of the dynamic cushion heel-ankle-foot orthosis as illustrated in FIGS. 1A-1D, according to an embodiment.

FIG. 9 illustrates a bottom plan view of the dynamic cushion heel-ankle-foot orthosis as illustrated in FIGS. 1A-1D, according to an embodiment. Some of the features in FIG. 9 are the same or similar to some of the features in FIG. 1A-8 as noted by the same reference numbers, unless expressly described otherwise. In one embodiment, an inner layer 42 of the heel portion 36 may be covered with a padding layer. In another embodiment, the inner layer 42 may include padding 50 and 52 depending on the needs of the user.

Figure 10:
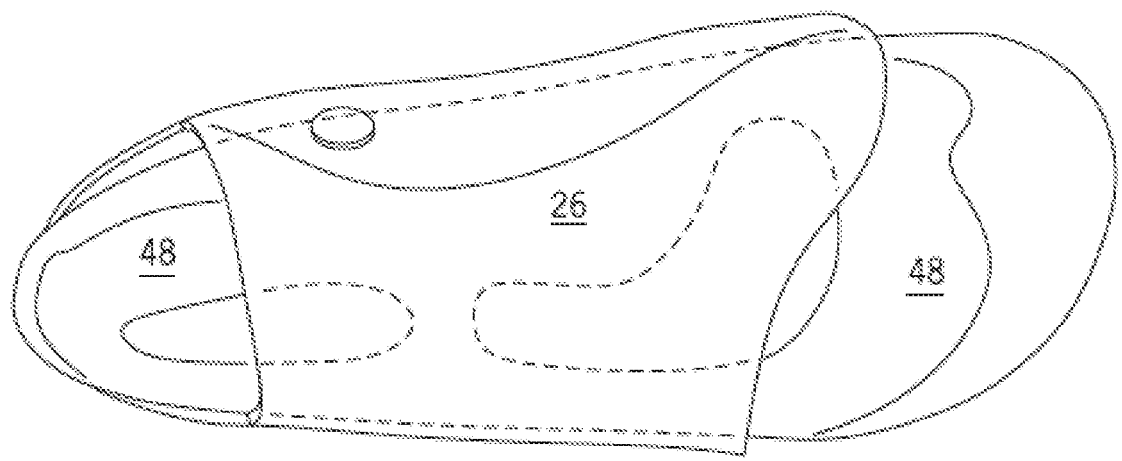
FIG. 10 illustrates another bottom plan view of the dynamic cushion heel-ankle-foot orthosis as illustrated in FIGS. 1A-1D, according to an embodiment.

FIG. 10 illustrates another bottom plan view of the dynamic cushion heel-ankle-foot orthosis as illustrated in FIGS. 1A-1D, according to an embodiment. Some of the features in FIG. 10 are the same or similar to some of the features in FIG. 1A-9 as noted by the same reference numbers, unless expressly described otherwise.

Figure 11:
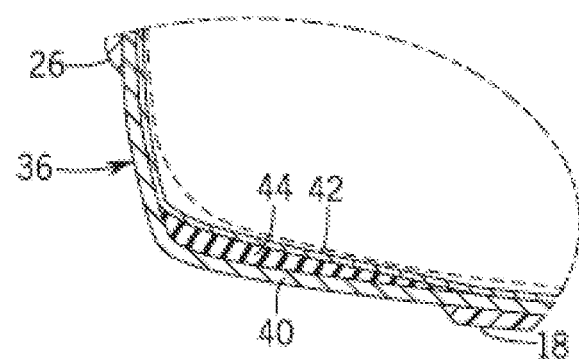
FIG. 11 illustrates a cross-sectional view of the dynamic cushion heel-ankle-foot orthosis as illustrated in FIGS. 1A-1D, according to an embodiment.

FIG. 11 illustrates a cross-sectional view of the dynamic cushion heel-ankle-foot orthosis as illustrated in FIGS. 1A-1D, according to an embodiment. Some of the features in FIG. 11 are the same or similar to some of the features in FIG. 1A-10 as noted by the same reference numbers, unless expressly described otherwise. The heel portion 36 may include an outer layer 40 fused to the inner layer 42. In one embodiment, the carbon foot plate 44 may be inserted between the outer layer 40 and the inner layer 42. In another embodiment, a cushion layer 46 may be fused to a portion of inner layer 42. In another embodiment, the carbon foot plate 44 may be the outermost layer with other layers as described above.

Figure 12:
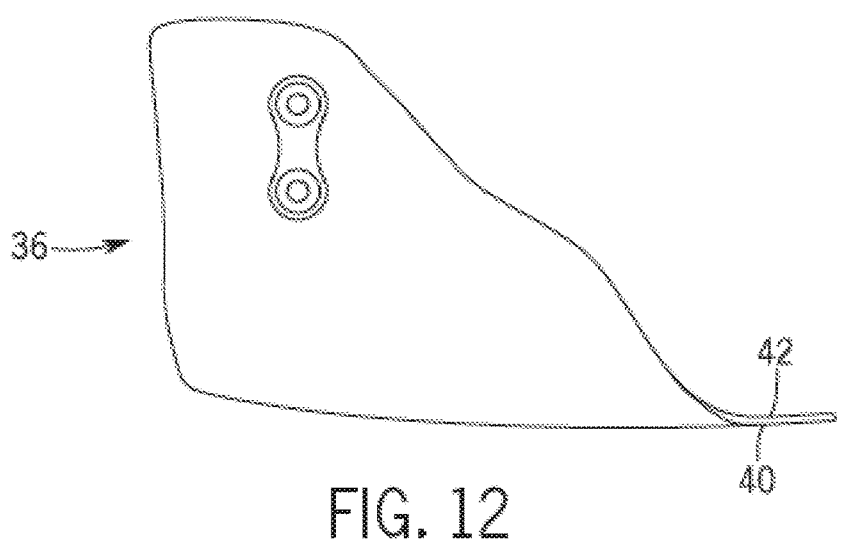
FIG. 12 illustrates a detail side elevation view of the dynamic cushion heel-ankle-foot orthosis as illustrated in FIGS. 1A-1D, according to an embodiment.

FIG. 12 illustrates a detail side elevation view of the dynamic cushion heel-ankle-foot orthosis as illustrated in FIGS. 1A-1D, according to an embodiment. Some of the features in FIG. 12 are the same or similar to some of the features in FIG. 1A-II as noted by the same reference numbers, unless expressly described otherwise.

Figure 13:
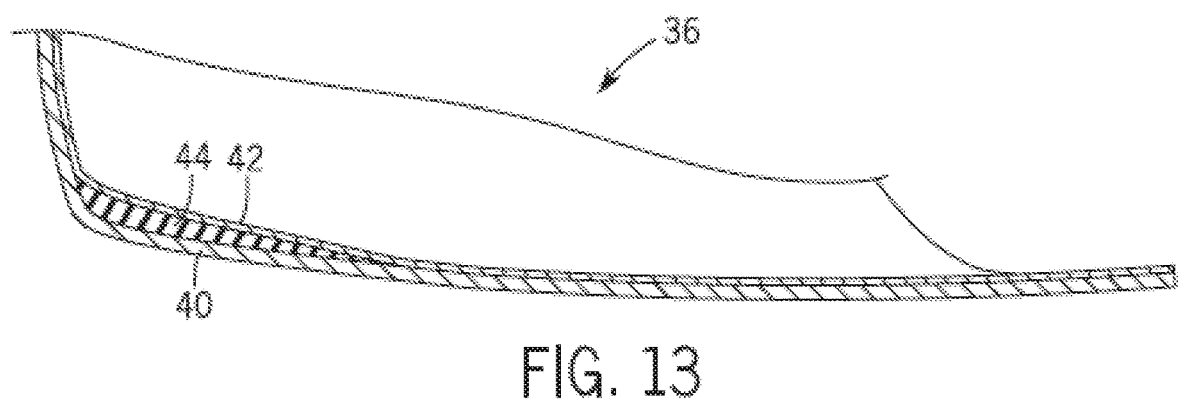
FIG. 13 illustrates another cross-sectional view of the dynamic cushion heel-ankle-foot orthosis as illustrated in FIGS. 1A-1D, according to an embodiment.

FIG. 13 illustrates another cross-sectional view of the dynamic cushion heel-ankle-foot orthosis as illustrated in FIGS. 1A-1D, according to an embodiment. Some of the features in FIG. 13 are the same or similar to some of the features in FIG. 1A-12 as noted by the same reference numbers, unless expressly described otherwise.

Figure 14:
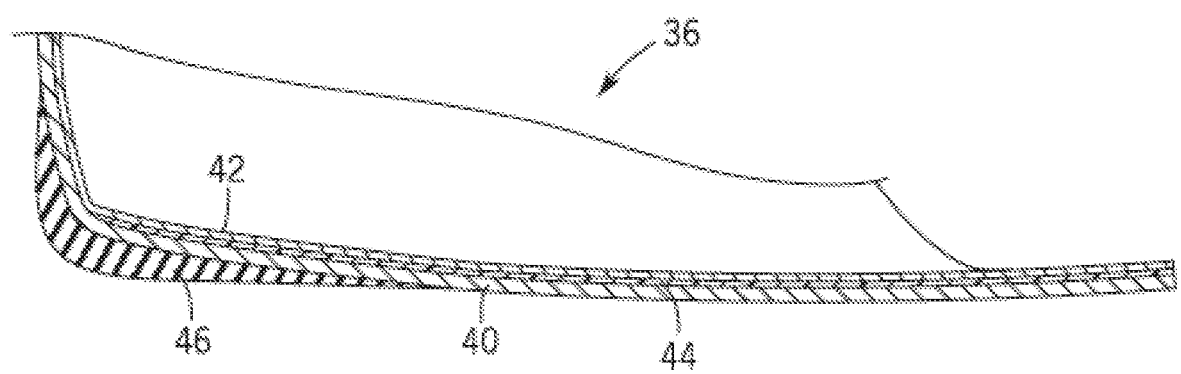
FIG. 14 illustrates another cross-sectional view of the dynamic cushion heel-ankle-foot orthosis as illustrated in FIGS. 1A-1D, according to an embodiment.

FIG. 14 illustrates another cross-sectional view of the dynamic cushion heel-ankle-foot orthosis as illustrated in FIGS. 1A-1D, according to an embodiment. Some of the features in FIG. 14 are the same or similar to some of the features in FIG. 1A-13 as noted by the same reference numbers, unless expressly described otherwise.

FIGS. 15-22 illustrate a process for making a stretch cord assembly 64. The process for making the stretch cord assembly 64 may include the following steps. The order of the steps is not intended to be limiting and may vary.

Figure 15:
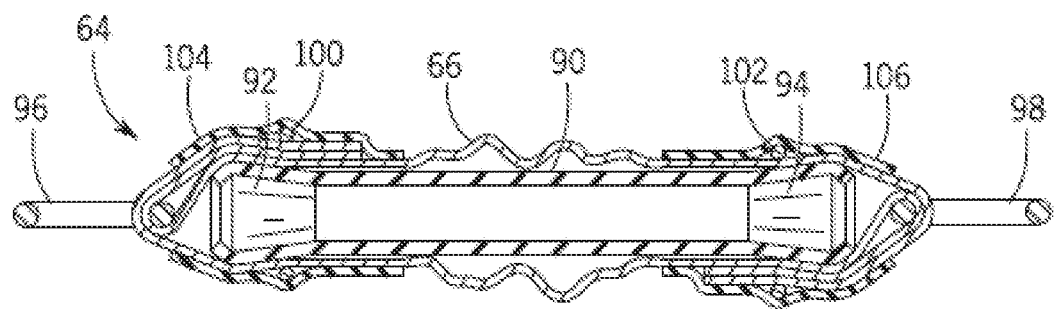
FIG. 15 illustrates a stretch cord assembly, according to an embodiment.

FIG. 15 illustrates a stretch cord assembly 64, according to an embodiment. Some of the features in FIG. 15 are the same or similar to some of the features in FIG. 1A-14 as noted by the same reference numbers, unless expressly described otherwise.

The stretch cord assembly 64 may include a hollow cord 90, a first retainer end 92, and second retainer end 94. The stretch cord assembly 64 may include a stretch cord sheath 66, a first ring 96, and second ring 98. The stretch cord assembly 64 may include a first clip 100 and second clip 102. The stretch cord assembly 64 may include a first rubber sleeve 104 and a second rubber sleeve 106. The stretch cord assembly 64 may include a first connector 72.

Figure 16:
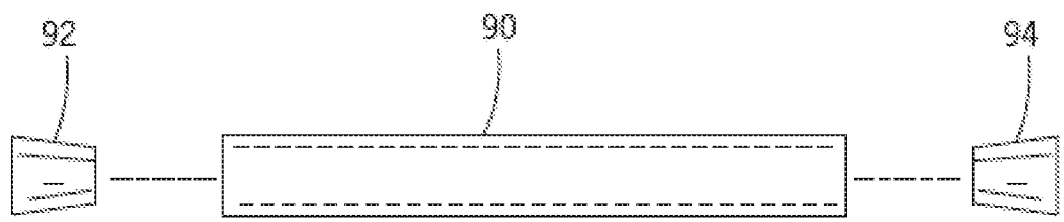
FIG. 16 illustrates a process step in constructing the stretch cord assembly in FIG. 15, according to an embodiment.

FIG. 16 illustrates a process step in constructing the stretch cord assembly 64 in FIG. 15, according to an embodiment. Some of the features in FIG. 16 are the same or similar to some of the features in FIG. 15 as noted by the same reference numbers, unless expressly described otherwise. As discussed above, the stretch cord assembly 64 may include a hollow cord 90. The process may include inserting first retainer end 92 and second retainer end 94 into hollow cord 90.

Figure 17:
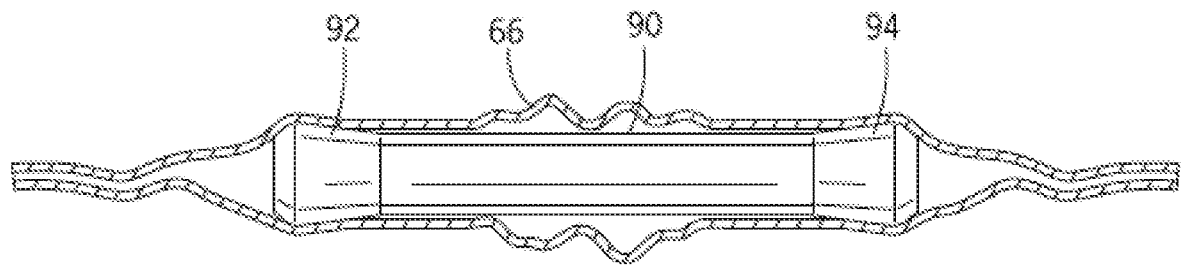
FIG. 17 illustrates another process step in constructing the stretch cord assembly in FIG. 15, according to an embodiment.

FIG. 17 illustrates another process step in constructing the stretch cord assembly 64 in FIG. 15, according to an embodiment. Some of the features in FIG. 17 are the same or similar to some of the features in FIG. 15-16 as noted by the same reference numbers, unless expressly described otherwise. The process may include sliding the stretch cord sheath 66 over the hollow cord 90.

Figure 18:
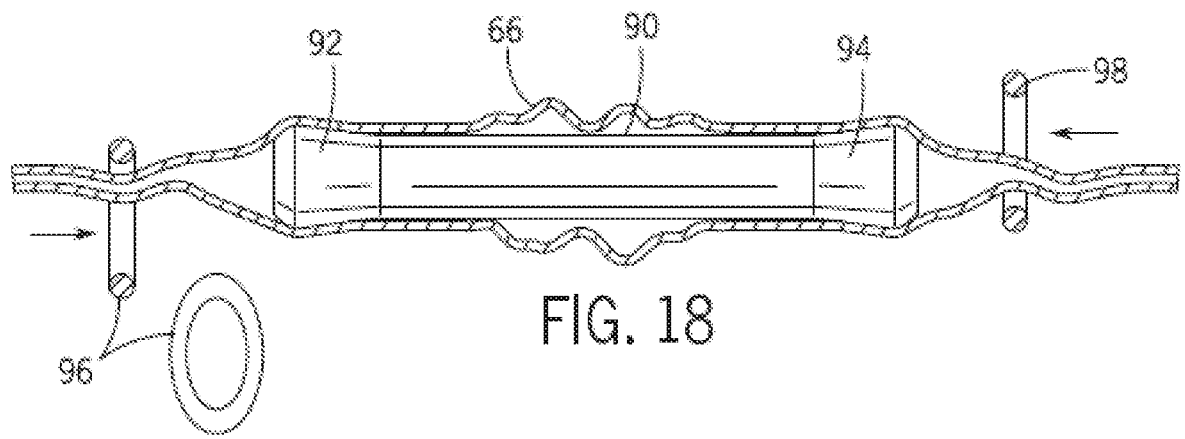
FIG. 18 illustrates another process step in constructing the stretch cord assembly in FIG. 15, according to an embodiment.

FIG. 18 illustrates another process step in constructing the stretch cord assembly 64 in FIG. 15, according to an embodiment. Some of the features in FIG. 18 are the same or similar to some of the features in FIG. 15-17 as noted by the same reference numbers, unless expressly described otherwise. The process may include wrapping the stretch cord sheath 66 around the first ring 96 and second ring 98.

Figure 19:
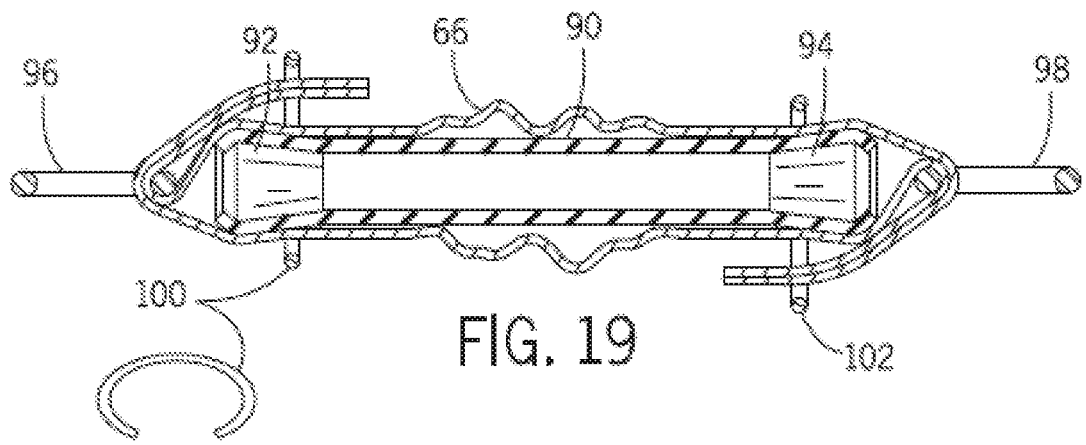
FIG. 19 illustrates another process step in constructing the stretch cord assembly in FIG. 15, according to an embodiment.

FIG. 19 illustrates another process step in constructing the stretch cord assembly 64 in FIG. 15, according to an embodiment. Some of the features in FIG. 19 are the same or similar to some of the features in FIG. 15-18 as noted by the same reference numbers, unless expressly described otherwise. The process may include holding the stretch cord sheath 66 with the first clip 100 and the second clip 102.

Figure 20:
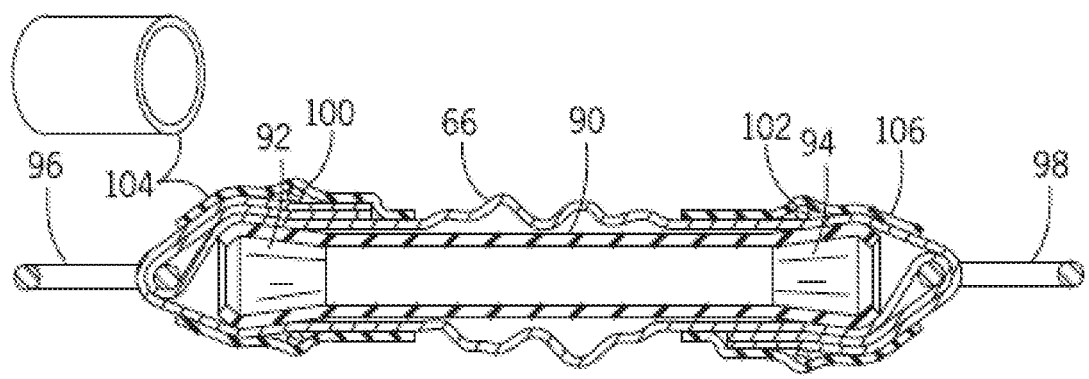
FIG. 20 illustrates another process step in constructing the stretch cord assembly in FIG. 15, according to an embodiment.

FIG. 20 illustrates another process step in constructing the stretch cord assembly 64 in FIG. 15, according to an embodiment. Some of the features in FIG. 20 are the same or similar to some of the features in FIG. 15-19 as noted by the same reference numbers, unless expressly described otherwise. The process may include covering the first clip 100 with first rubber sleeve 104 and covering the second clip 102 with second rubber sleeve 106.

Figure 21:
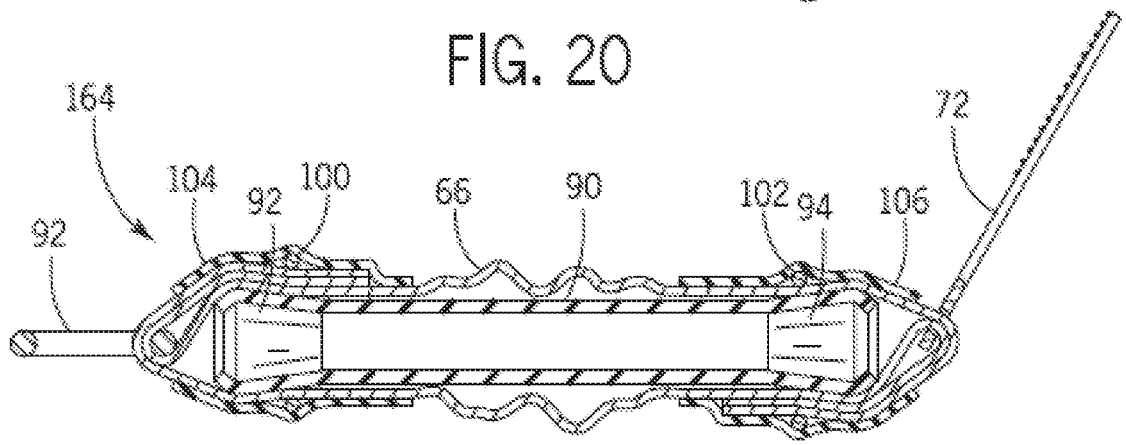
FIG. 21 illustrates a cross-sectional view of a stretch cord assembly, according to an embodiment.

FIG. 21 illustrates a cross-sectional view of a stretch cord assembly 64, according to an embodiment. Some of the features in FIG. 21 are the same or similar to some of the features in FIG. 15-20 as noted by the same reference numbers, unless expressly described otherwise. In one embodiment, the second ring 98 of the stretch cord assembly 64 may be replaced with first connector 72.

Figure 22:
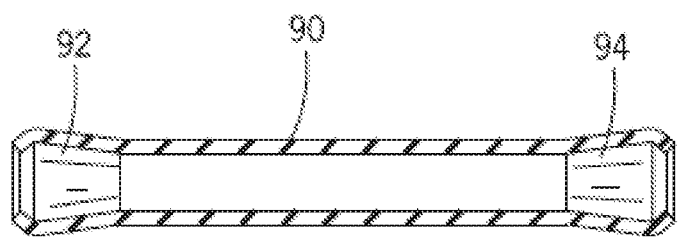
FIG. 22 illustrates a process step in constructing a stretch cord assembly according to an embodiment.

FIG. 22 illustrates a process step in constructing a stretch cord assembly 64 according to an embodiment. Some of the features in FIG. 22 are the same or similar to some of the features in FIG. 15-21 as noted by the same reference numbers, unless expressly described otherwise. The hollow cord 90 may be wrapped around first retainer end 92 and second retainer end 94.

Figure 23:
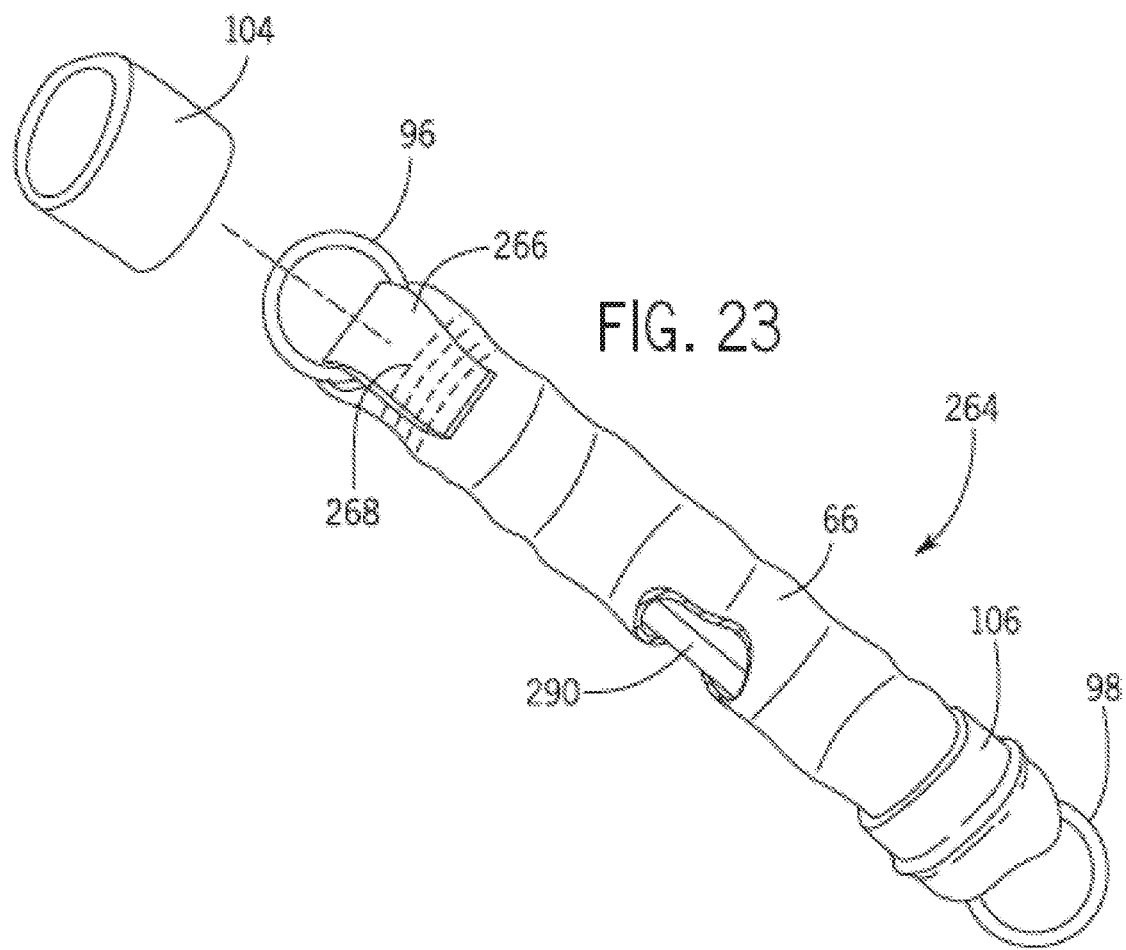
FIG. 23 illustrate a stretch cord assembly that includes an internal cord, according to an embodiment.

FIG. 23 illustrate a stretch cord assembly 264 that includes an internal cord 290, according to an embodiment. Some of the features in FIG. 23 are the same or similar to some of the features in FIG. 15-22 as noted by the same reference numbers, unless expressly described otherwise. The internal cord 290 may be a shock cord, an elastic cord, a bungee cord, and so forth. In one embodiment, a process of assembling the stretch cord assembly 264 may include sliding the stretch cord sheath 66 over the internal cord 290. The process of assembling the stretch cord assembly 264 may include wrapping the first strap 266 around a first ring 96. The process of assembling the stretch cord assembly 264 may include sewing the first strap 266 to the stretch cord sheath 66 with stitching 268. In another embodiment, the first strap 266 may be a non-stretch fabric that does not deform when under a load. The process of assembling the stretch cord assembly 264 may include wrapping the stretch cord sheath 66 around a second ring 98. In one example, the second clip 102 may be fit over the stretch cord sheath 66. The second clip 102 may provide additional strength and structural integrity to the stretch cord assembly 264. In another embodiment, a first rubber sleeve 104 may cover at least a portion of the first strap 266, such as covering the stitching 268. In another embodiment, the second rubber sleeve 106 may cover at least a portion of the stretch cord sheath 66.

Figure 24:
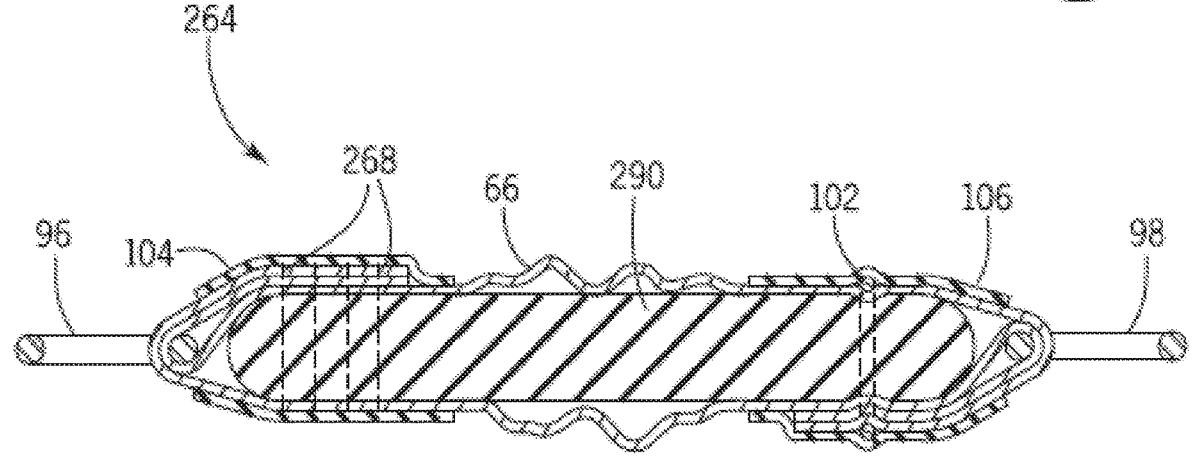
FIG. 24 illustrates a cross-sectional view of the stretch cord assembly in FIG. 23, according to an embodiment.

FIG. 24 illustrates a cross-sectional view of the stretch cord assembly 264 in FIG. 23, according to an embodiment. Some of the features in FIG. 24 are the same or similar to some of the features in FIG. 15-23 as noted by the same reference numbers, unless expressly described otherwise.

Figure 25A:
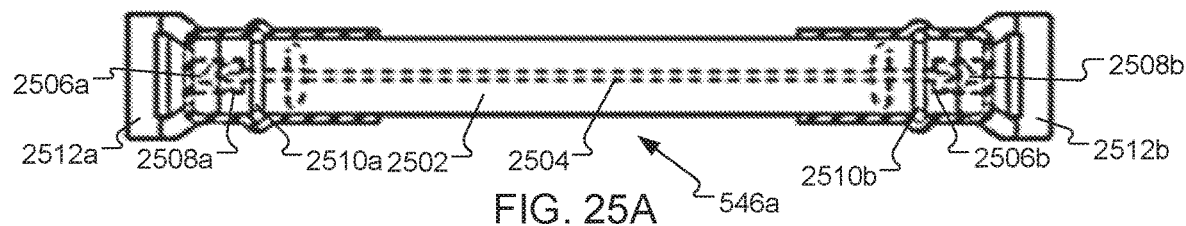
FIG. 25A illustrates stretch cord assembly, according to an embodiment.

FIGS. 25A-E illustrate a variety of stretch cord assemblies 546a-546d to attach to the dynamic cushion heel-ankle-foot orthosis 10 or 200 in FIGS. 1A-1D. FIG. 25A illustrates the stretch cord assembly 546a, according to an embodiment. The stretch cord assembly 546a may include a band 2502, an internal cord 2504, a first buckle end, and a second buckle end. In one embodiment, the stretch cord assembly 546a may include first buckle end with a first internal cord end 2506a, a first pocket 2508a, a first ring 2510*a*, and a first buckle 2512*a*. In another embodiment, the stretch cord assembly 546*a* may include the second buckle end with a second internal cord end 2506*b*, a second pocket 2508*b*, a second ring 2510*b*, and a second buckle 2512*b*. FIG. 25A illustrates that the first buckle end and the second buckle end may include the same features and may be mirror images of each other.

The band 2502 may be a material with a defined length. In one embodiment, the material of the band 2502 may be leather, plastic, rubber, fabric, and so forth. In another embodiment, the material may be a stretchable material, such as cotton, Spandex®, fleece, Selvedge®, and so forth. When the material of the band 2502 is a stretchable material, the band 2502 may expand to a first length and contract to a second length. In another embodiment, the band 2502 may be a tube, a band, a cord, and so forth. In another embodiment, the band 2502 may be at least partially hollow or include a channel that extends the length of the band 2502.

The band 2502 may also include an internal channel, where the internal cord 2504 may extend from a first end of the band 2502 to a second end of the band 2502. The band 2502 may also include a first pocket 2508*a* at the first end of the band 2502 and a second pocket 2508*b* at a second end of the band 2502. The first pocket 2508*a* may be configured to receive a first end 2506*a* of the internal cord 2504. In one embodiment, the internal cord 2504 may be made of non-stretchable material and the first pocket 2508*a* may restrict or limit the length that the internal cord 2504 may extend or contract at the first end of the band 2502. For example, the first end 2508*a* of the internal cord 2504 may extend to an outer edge of the first pocket 2508*a* and may contract in length to the inner edge of the first pocket 2508*a*. The second pocket 2508*b* may be configured to receive a second end 2508*b* of the internal cord 2504. The second pocket 2508*b* may restrict or limit the length that the internal cord 2504 may extend or contract at the second end of the band 2502. For example, the second end 2506*b* of the internal cord 2504 may extend to an outer edge of the second pocket 2508*b* and may contract in length to the inner edge of the second pocket 2508*b*.

The configuration band 2502 with the internal cord 2504 may restrict a length that the stretch cord assembly 546*a* may extend to. For example, the internal cord 2504 may have a maximum length that the internal cord 2504 may extend to within the first pocket 2508*a* and the second pocket 2508*b*. Restricting the length of the stretch cord assembly 546*a* may restrict an amount the dynamic cushion heel-ankle-foot orthoses as illustrated in FIGS. 1A-1D may rotate or move.

The stretch cord assembly 546*a* may include the first ring 2510*a* and the second ring 2510*b*. In one embodiment, the first ring 2510*a* may reinforce the first pocket 2508*a* to keep the first end 2506*a* of the internal cord 2504 from contracting beyond a first defined point. In another embodiment, the second ring 2510*b* may reinforce the second pocket 2508*b* to keep the second end 2506*b* of the internal cord 2504 from contracting beyond a second defined point.

The stretch cord assembly 546*a* may include the first buckle 2512*a* at the first end of the band 2502 and a second buckle 2512*b* on the second end of the band 2502. The first buckle 2512*a* and the second buckle 2512*b* may be used to attach the stretch cord assembly 546*a* to various buckles, attachments, fasteners, parts, or portions of the dynamic cushion heel-ankle-foot orthoses as illustrated in FIGS. 1A-1D.

Figure 25B:
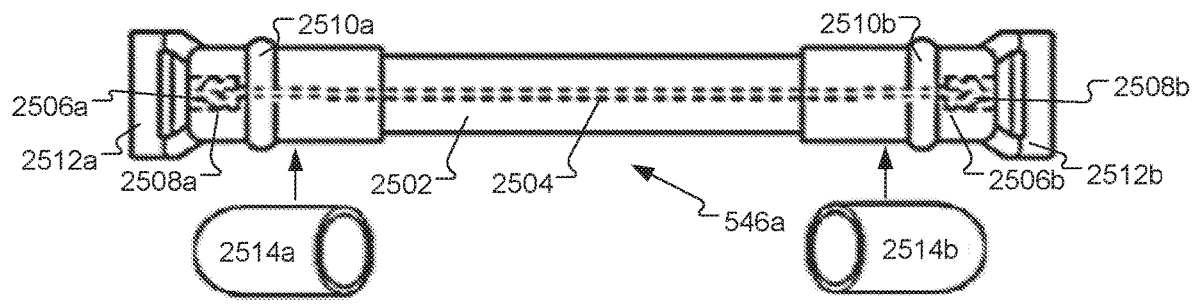
FIG. 25B illustrates the stretch cord assembly with covers, according to an embodiment.

FIG. 25B illustrates the stretch cord assembly 546*a* with covers 2514*a* and 2514*b*, according to an embodiment. Some of the features in FIG. 25B are the same or similar to some of the features in FIG. 25A as noted by the same reference numbers, unless expressly described otherwise. In one embodiment, a first cover 2514*a* may be attached to the first end of the band 2502 to cover, protect, and/hide the portion of the first end of the band 2502 and the first ring 2510*a*. In one embodiment, a second cover 2514*b* may be attached to the second end of the band 2502 to cover, protect, and/hide the portion of the second end of the band 2502 and the second ring 2510*b*.

Figure 25C:
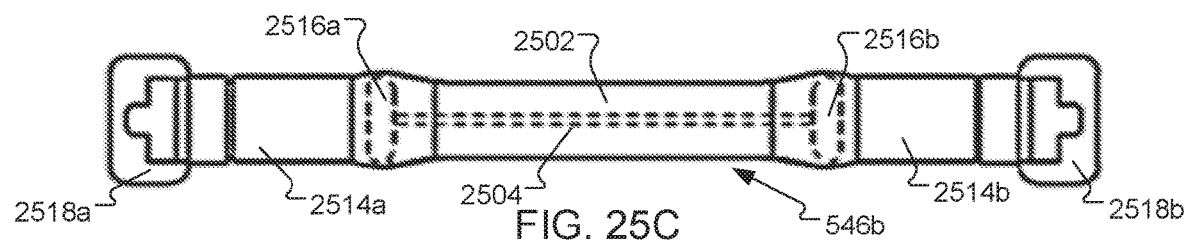
FIG. 25C illustrates the stretch cord assembly with the internal cord with integrated ends, according to an embodiment.

FIG. 25C illustrates the stretch cord assembly 546*b* with the internal cord 2504 with integrated ends 2516*a* and 2516*b*, according to an embodiment. Some of the features in FIG. 25C are the same or similar to some of the features in FIGS. 25A-B as noted by the same reference numbers, unless expressly described otherwise. In one embodiment, the internal cord 2504 may include a first integrated end 2516*a* that is integrated into a portion of the first end of the band 2502. In another embodiment, the internal cord 2504 may include a second integrated end 2516*b* that is integrated into a portion of the second end of the band 2502. The first integrated end 2516*a* and the second integrated end 2516*b* may be fixed to internal portions of the band 2502 such that the band 2502 may not expand or contract.

In another embodiment, the first buckle 2518*a* may be attached to the first end of the band 2502 and the second buckle 2518*b* may be attached to the second end of the band 2502. The first buckle 2518*a* and the second buckle 2518*b* may be adjustably attached to various buckles, attachments, fasteners, parts, or portions of the dynamic cushion heel-ankle-foot orthoses as illustrated in FIGS. 1A-1D.

Figure 25D:
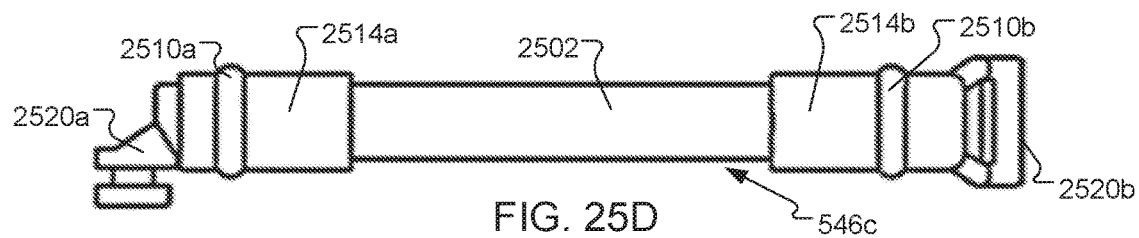
FIG. 25D illustrates the stretch cord assembly a first buckle and a second buckle, according to an embodiment.

FIG. 25D illustrates the stretch cord assembly 546*c* a first buckle 2520*a* and a second buckle 2520*b*, according to an embodiment. Some of the features in FIG. 25D are the same or similar to some of the features in FIGS. 25A-C as noted by the same reference numbers, unless expressly described otherwise. In one embodiment, the stretch cord assembly 546*c* may not include the internal cord 2504 and the band 2502 may be made of non-stretchable material. The stretch cord assembly 546*c* may also include a first buckle 2520*a* that is attached to the first end of the band 2502. For example, the first buckle 2520*a* may be attached to the first end of the band 2502 by an adhesive, welding, heat, and so forth. The first end of the band 2502 and/or the first buckle 2520*a* may be covered by the first cover 2514*a*. In one embodiment, the first cover 2514*a* may be fastened to the band 2502 by the first ring 2510*a*.

The stretch cord assembly 546*c* may also include a second buckle 2520*b* that is attached to the second end of the band 2502. For example, the second buckle 2520*b* may be attached to the second end of the band 2502 by an adhesive, welding, heat, and so forth. The second end of the band 2502 and/or the second buckle 2520*b* may be covered by the second cover 2514*b*. In one embodiment, the second cover 2514*b* may be fastened to the band 2502 by the second ring 2510*b*. In one embodiment, the first buckle 2520*a* may be the same type of buckle as the second buckle 2520*b*. In another embodiment, the first buckle 2520*a* may be a different type of buckle than the second buckle 2520*b*. The first buckle 2520*a* and/or the second buckle 2520 may be adjustably attached to various buckles, attachments, fasteners, parts, or portions of the dynamic cushion heel-ankle-foot orthoses as illustrated in FIGS. 1A-1D. For example, as discussed below, the first buckle 2520*a* may be inserted into different slots in the leg calf shell 12 to adjust the length of the stretch cord assembly 546*c* and thereby loosen to tighten different portions of the dynamic cushion heel-ankle-foot orthoses as illustrated in FIGS. 1A-1D.

Figure 25E:
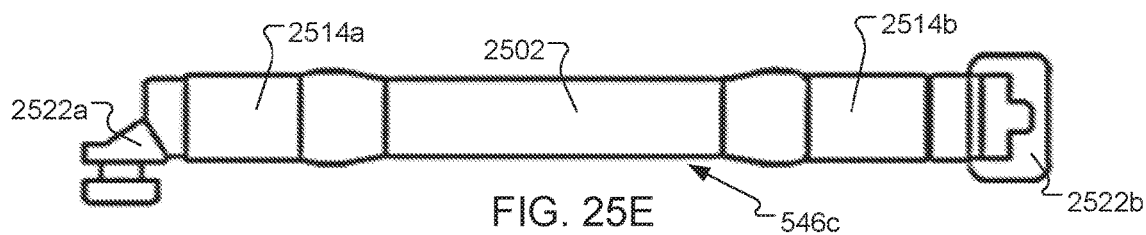
FIG. 25E illustrates the stretch cord assembly a first buckle and a second buckle, according to an embodiment.

FIG. 25E illustrates the stretch cord assembly 546c, a first buckle 2522a, and a second buckle 2522b, according to an embodiment. Some of the features in FIG. 25E are the same or similar to some of the features in FIGS. 25A-D as noted by the same reference numbers, unless expressly described otherwise. In one embodiment, the first buckle 2522a and the second buckle 2522b may be integrally attached to the band 2502. For example, a band 2502, the first buckle 2522a, and the second buckle 2522b may be formed out of a single piece of material, such as via molding, casting, or three dimensional (3D) printing. In another embodiment, the first buckle 2522a may be attached to the first end of the band 2502 by the first cover 2514a and the second buckle 2522b may be attached to the second end of the band 2502 by the second cover 2514b.

FIG. 26A-D illustrate a process for making a stretch cord assembly 564a. The process for making the stretch cord assembly 564a may include the following steps. The order of the steps is not intended to be limiting and may vary. A similar process may be used for making the stretch cord assembly 564b in FIG. 25C and/stretch cord assembly 564c in FIGS. 25D-E.

Figure 26A:
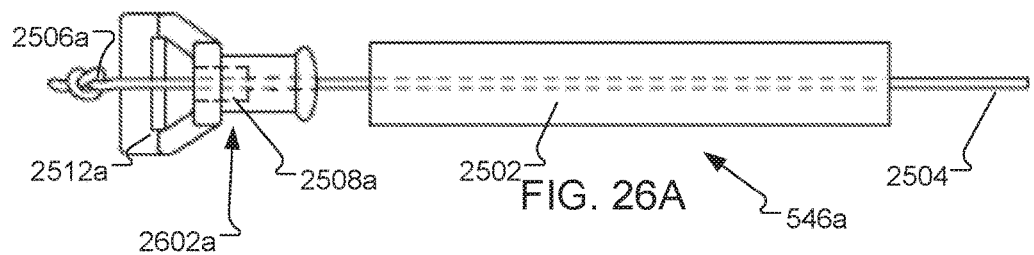
FIG. 26A illustrates a process step of assembling a portion of the stretch cord assembly, according to an embodiment.

FIG. 26A illustrates a process step of assembling a portion of the stretch cord assembly 564a, according to an embodiment. Some of the features in FIG. 26A are the same or similar to some of the features in FIG. 25A-B as noted by the same reference numbers, unless expressly described otherwise.

The stretch cord assembly 564a may include the first buckle 2512a, the internal cord 2505, and a first retainer end 2602a. The first retainer end 2602a may include a portion of the band 2502 with the first pocket 2508a. The internal cord 2504 may be inserted through the first pocket 2508a, the portion of the band 2502 of the first retainer end 2602a, and the remaining portion of the band 2502. The first buckle 2512a may also be attached to the portion of the band 2502 of the first retainer end 2602a.

Figure 26B:
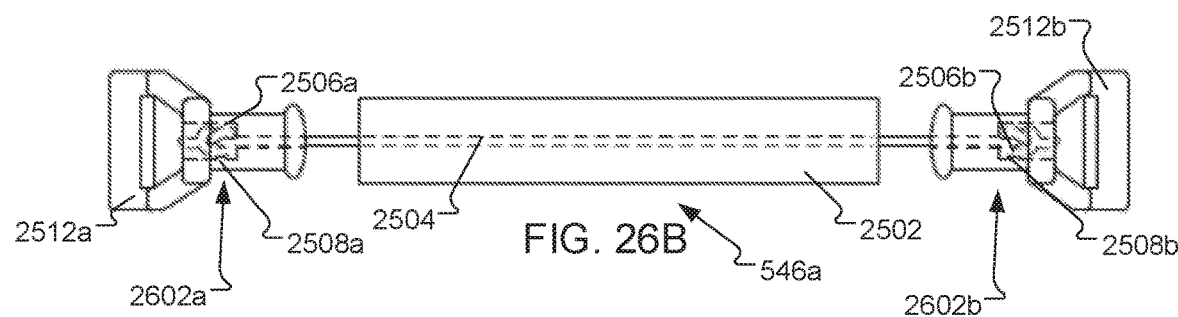
FIG. 26B illustrates another process step of assembling a portion of the stretch cord assembly, according to an embodiment.

FIG. 26B illustrates another process step of assembling a portion of the stretch cord assembly 564a, according to an embodiment. Some of the features in FIG. 26B are the same or similar to some of the features in FIGS. 25A-B and 26A as noted by the same reference numbers, unless expressly described otherwise. As discussed above, the stretch cord assembly 564a may include the first buckle 2512a, the internal cord 2504, and a first retainer end 2602a. The stretch cord assembly 564a may also include the second buckle 2512b and a second retainer end 2602b. The second retainer end 2602b may include a second portion of the band 2502 with the second pocket 2508b. The internal cord 2504 may be inserted into the second portion of the band 2502 of the second retainer end 2602b toward the second pocket 2508b. The second buckle 2512b may also be attached to the second portion of the band 2502 of the second retainer end 2602b.

Figure 26C:
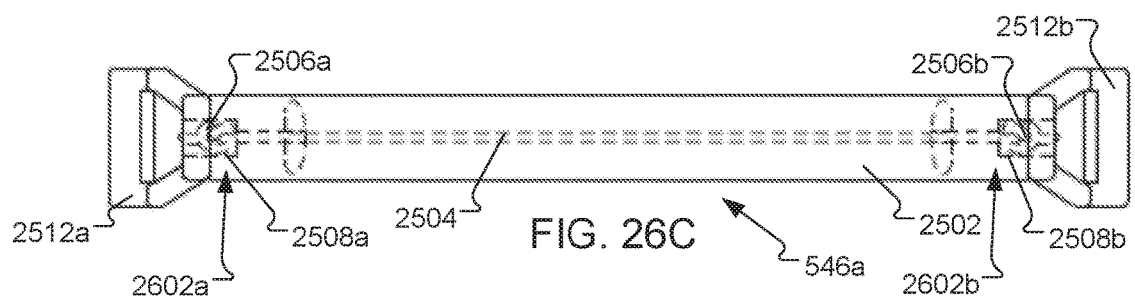
FIG. 26C illustrates another process step of assembling a portion of the stretch cord assembly, according to an embodiment.

FIG. 26C illustrates another process step of assembling a portion of the stretch cord assembly 564a, according to an embodiment. Some of the features in FIG. 26C are the same or similar to some of the features in FIG. 25A-26B as noted by the same reference numbers, unless expressly described otherwise. When the internal cord 2504 is attached to the first retainer end 2602a and the second retainer end 2602b, the internal cord 2504 may contract to pull the first buckle 2512a to a first end of the band 2502 and the second buckle 2512b to a second end of the band 2502.

Figure 26D:
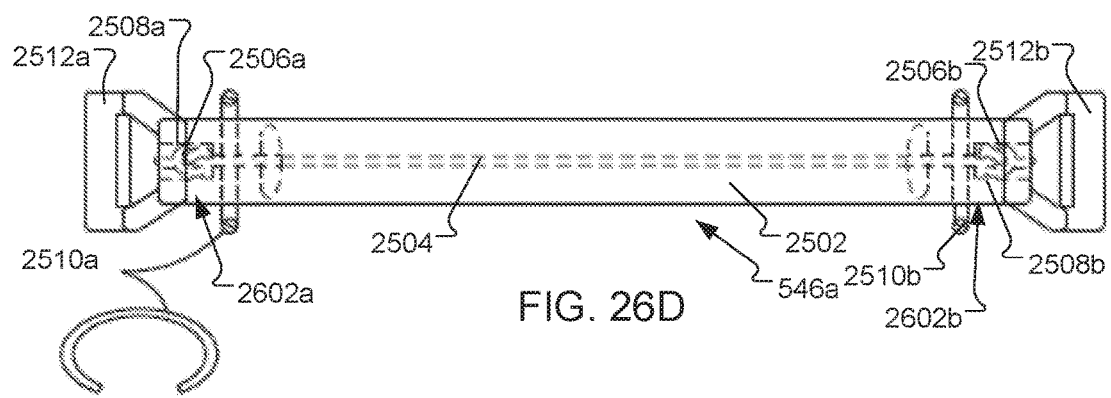
FIG. 26D illustrates another process step of assembling a portion of the stretch cord assembly, according to an embodiment.

FIG. 26D illustrates another process step of assembling a portion of the stretch cord assembly 564a, according to an embodiment. Some of the features in FIG. 26D are the same or similar to some of the features in FIG. 25A-26C as noted by the same reference numbers, unless expressly described otherwise. When the internal cord 2504 has contracted it pulls the first buckle 2512a to a first end of the band 2502 and the second buckle 2512b to a second end of the band 2502. The first ring 2510a may be attached approximate to the first end of the band 2502 and the second ring 2510b may be attached approximate to the second end of the band 2502 to keep the second retainer end 2602b in place so that the stretch cord assembly 564a extends and contracts within a defined length range.

Figure 27A:
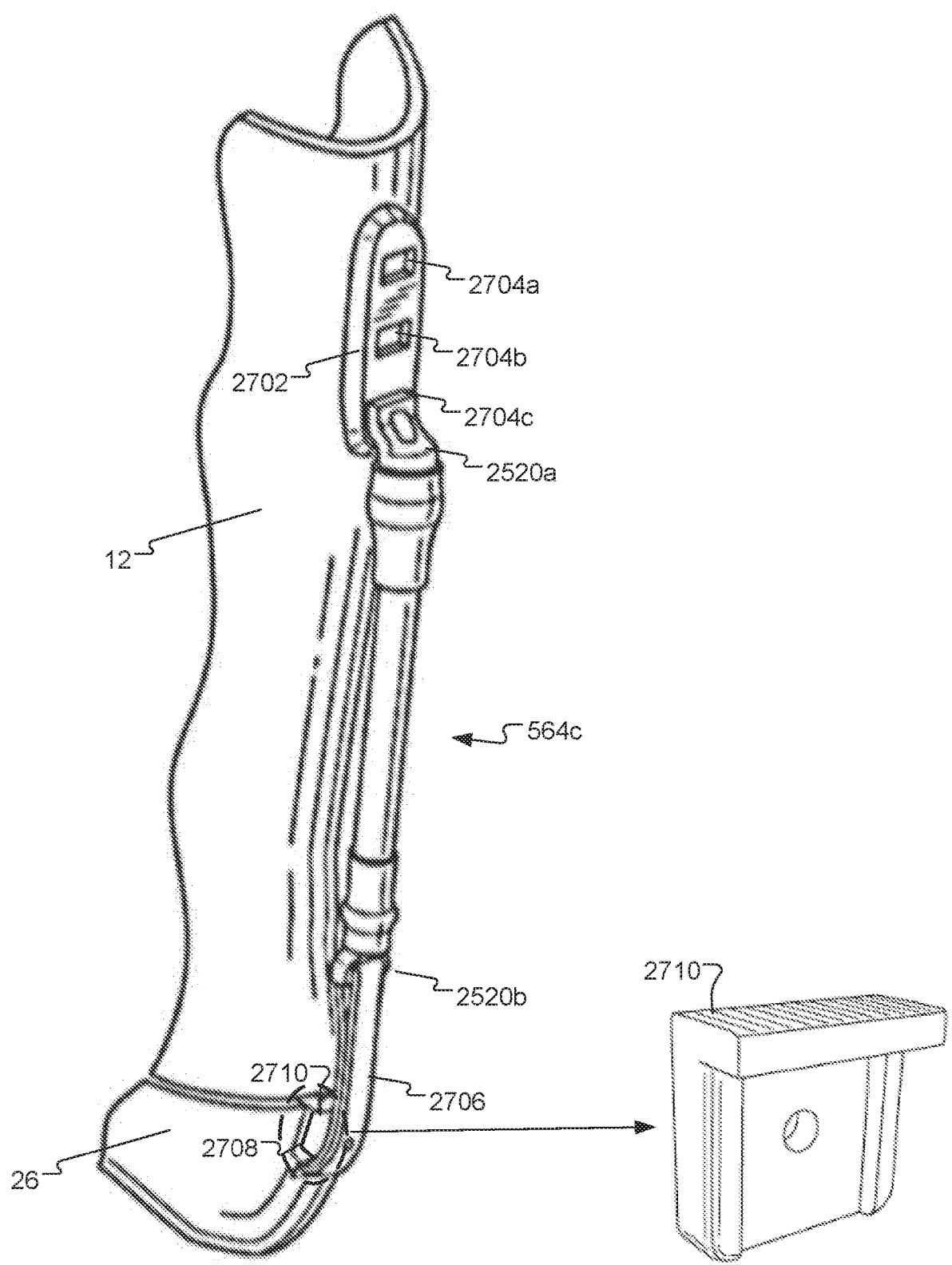
FIG. 27A illustrates a back portion of the leg calf shell and a heel portion of the boot shell connected together by the stretch cord assembly, according to an embodiment.

FIG. 27A illustrates a back portion of the leg calf shell 12 and a heel portion of the boot shell 26 connected together by the stretch cord assembly 564c, according to an embodiment. Some of the features in FIG. 27A are the same or similar to some of the features in FIGS. 1A-D and 25A-25E as noted by the same reference numbers, unless expressly described otherwise. As discussed above, the stretch cord assembly 564c may connect the back portion of the leg calf shell 12 and the heel portion of the boot shell 26. In one embodiment, the back portion of the leg calf shell 12 may include a buckle attachment 2702 with one or more slots to receive the first buckle 2520a. In one example, the buckle attachment 2702 may include a first slot 2704a, a second slot 2704b, and a third slot 2704c. The first buckle 2520a may include a block end that may be configured to be inserted into one of the slots 2704a-c. In one example, the block end of the first buckle 2520a may be inserted into the first slot 2704a and remain attached to the buckle attachment 2702 via a friction fit. In another example, the block end of the first buckle 2520a may be rotated to a first orientation to be inserted into the first slot 2704a and then rotated to a second orientation to lock the block end in place so that it is fastened to the buckle attachment 2702.

The heel portion of the boot shell 26 may include a strap 2706 connected to the heel portion by a fastener 2708. The strap 2706 may be attached to the second buckle 2520b of the stretch cord assembly 564c. In one embodiment, the strap 2706 may be fixedly fastened to the second buckle 2520b such that the strap 2706 may not be removed from the second buckle 2520b. The strap 2706 may then be fastened to the fastener 2708 by a friction fit, a rivet, a screw, epoxy, an adhesive, a clamp, or another type of fastener. In another embodiment, the strap 2706 may be fixedly fastened to the fastener 2708 such that the strap 2706 may not be removed from the fastener 2708. The strap 2706 may then be fastened to the second buckle 2520b by a friction fit, a rivet, a screw, epoxy, an adhesive, a clamp, or another type of fastener. In another embodiment, a first end of the strap 2706 may be fastened to the fastener 2708 and a second end of the strap may be inserted through an opening of the second buckle 2520b and then also fastened to the fastener 2708. In another embodiment, the fastener 2708 may include a portion 2710 that may extend from the fastener 2708 to fit between the heel portion of the boot shell 26 and the back portion of the leg calf shell 12 to separate the heel portion of the boot shell 26 from the back portion of the leg calf shell 12.

Figure 27B:
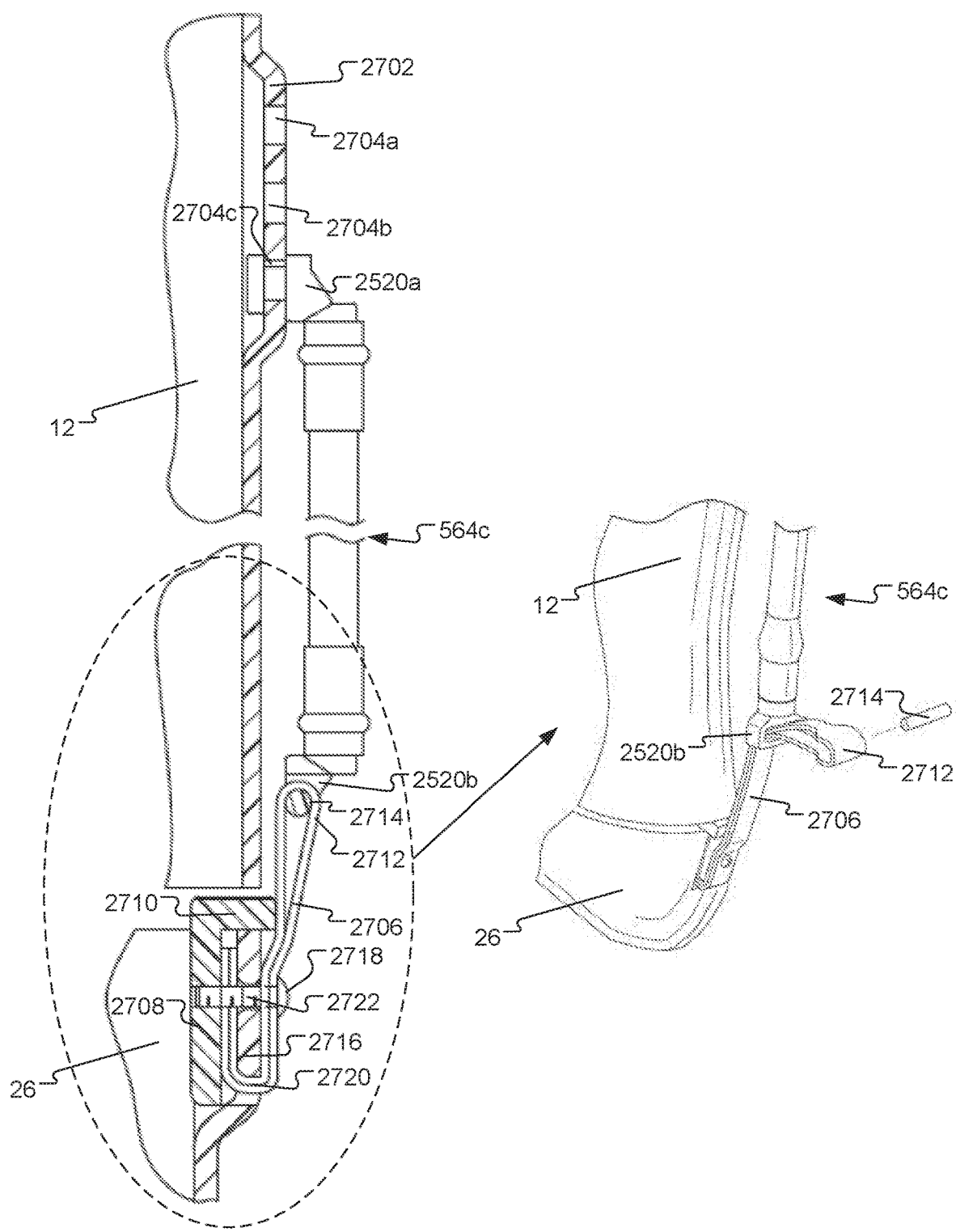
FIG. 27B illustrates an exposed view of the back portion of the leg calf shell and a heel portion of the boot shell connected together by the stretch cord assembly, according to an embodiment.

FIG. 27B illustrates an exposed view of the back portion of the leg calf shell 12 and a heel portion of the boot shell 26 connected together by the stretch cord assembly 564c, according to an embodiment. Some of the features in FIG. 27B are the same or similar to some of the features in FIGS. 1A-D, 25A-25E, and 27A as noted by the same reference numbers, unless expressly described otherwise.

As discussed above, the stretch cord assembly 564c may be connected to the strap 2706 in order to connect the back portion of the leg calf shell 12 to the heel portion of the boot shell 26. In one embodiment, a first end of the strap 2706 and a second end of the strap 2706 may be fastened to the fasteners 2708 to form a loop end 2712. The loop end 2712 of the strap 2706 may be inserted into an opening of the second buckle 2520b. To secure the strap 2706 to the second buckle 2520b, a peg 2714 may be inserted into the loop end 2712 of the strap 2706 so that a diameter of the loop end 2712 is greater in size than the opening of the second buckle 2520b such that the loop end 2712 may not go back through the opening of the second buckle 2520b. The configuration of the loop end 2712 with the peg 2714 may allow the stretch cord assembly 564c to be removably attached to the heel portion of the boot shell 26. For example, when the page 2710 is removed from the loop end 2712, the loop end 2712 may be disconnected from the second buckle and the first buckle 2520a may be removed from the first slot 2704a to allow the stretch cord assembly 564c to be removed and/or replaced.

In one embodiment, to connect the strap 2706 to the heel portion of the boot shell 26, the fastener 2708 may include a locking portion 2716 that may be attached to the fastener 2708. The locking portion 2716 may include a slot 2720 to receive an end of the strap 2706 that connects to the heel portion of the boot shell 26 and an opening 2722 to receive a holder 2718. The holder 2718 may be a rivet, a bolt, a screw, a clasp, a snap, and so forth. In one embodiment, once the end of the strap 2706 that connects to the heel portion of the boot shell 26 is inserted into the slot 2720, the holder 2718 may be inserted into the opening 2722 to secure the strap 2706 to the heel portion of the boot shell 26. The thick of the portion 2710 may vary to increase or decrease an amount of separate between the bottom of the leg calf shell 12 and the top of the boot shell 26. For example, as the thickness of the portion 2710 increase, the separation between the bottom of the leg calf shell 12 and the top of the boot shell 26 may increase. In another embodiment, the holder 2718 may connect directly to the back of the boot shell 26 instead of connecting to the fastener 2708.

FIG. 28A-C illustrate a process for making the buckle attachment 2702, according to an embodiment. The process for making the buckle attachment 2702 may include the following steps. The order of the steps is not intended to be limiting and may vary. Some of the features in FIG. 28A-C are the same or similar to some of the features in FIG. 27A-B as noted by the same reference numbers, unless expressly described otherwise.

FIG. 28A illustrates a process step of forming the buckle attachment 2702 into the leg calf shell 12, according to an embodiment. In one embodiment, to form the buckle attachment 2702, the leg calf shell 12 may be plaster or fiberglass. For example, the leg calf shell 12 may be a shell formed using a plaster or fiberglass mold for a cast of the leg. As the plaster or fiberglass is forming, a fastener form 2802 with protrusions may be used to form slots. For example, the fastener form 2802 may include a first protrusion 2804a, a second protrusion 2804b, and a third protrusion 2804c. The number of protrusions and slots are not intended to be limiting. The fastener form 2802 may include a single protrusion or multiple protrusions and the buckle attachment 2702 may include a single slot or multiple slots.

FIG. 28B illustrates a process step of pressing the fastener form 2802 into the leg calf shell 12 to form the buckle attachment 2702, according to an embodiment. As the plaster or fiberglass is being formed or drying, the fastener form 2802 may be pressed into the plaster or fiberglass of the leg calf shell 12 to form the corresponding slots 2804a-c into the leg calf shell 12.

FIG. 28C illustrates a process step of removing the fastener form 2802 from the leg calf shell 12 to form the buckle attachment 2702, according to an embodiment. In one example, the first protrusion 2804a of the fastener form 2802 may be pressed into the leg calf shell 12 to form the first slot 2704a, the second protrusion 2804b of the fastener form 2802 may be pressed into the leg calf shell 12 to form the second slot 2704b, and the third protrusion 2804c of the fastener form 2802 may be pressed into the leg calf shell 12 to form the third slot 2704c. Once the slots 2704a-c have been formed, the fastener form 2802 may be removed from the leg calf shell 12.

FIG. 29A-D illustrate a process for making the locking portion 2716 as illustrated in FIG. 27B, according to an embodiment. The process for making the buckle attachment 2702 may include the following steps. The order of the steps is not intended to be limiting and may vary. Some of the features in FIG. 29A-D are the same or similar to some of the features in FIG. 27A-B as noted by the same reference numbers, unless expressly described otherwise.

FIG. 29A illustrates a process step of forming the locking portion 2716, according to an embodiment. In one embodiment, to form the locking portion 2716, the locking portion 2716 may be a formable material such as plastic, rubber, polyurethane, and so forth. As the formable material of the locking portion 2716 is forming, a locking form 2902 with protrusions may be used to form slots and openings. For example, the locking form 2902 may include a top protrusion 2904, a middle protrusion 2906, and a bottom protrusion 2908.

FIG. 29B illustrates a process step of forming the locking form 2902, according to an embodiment. To form the locking portion 2716, formable material 2910 may be pressed against the locking form 2902.

FIG. 29C illustrates a process step of pressing the locking form 2902 into formable material 2910 to form the locking portion 2716, according to an embodiment. As the formable material 2910 is being formed or drying, the fastener form 2802 may be pressed into the formable material 2910 to form the slot 2720 and the opening 2722 into the locking portion 2716 as illustrated in FIG. 27B. In one example, the top protrusion 2904 of the locking form 2902 may be placed above the formable material 2910 to align the locking form 2902 with the formable material 2910. In another example, as the formable material 2910 is pressed into the locking form 2902 the middle protrusion 2906 may be pressed into the formable material 2910 to form the opening 2722 and the bottom protrusion 2908 may be pressed into the formable material 2910 to form the slot 2720 in FIG. 27B.

FIG. 29D illustrates a process step of removing the locking form 2902 from the formable material 2910 to form the locking portion 2716, according to an embodiment. Once the slot 2720 and the opening 2722 have been formed, the locking form 2902 may be removed from the formable material 2910 and the locking portion 2716 may be formed. The number of protrusions, slots, and holes are not intended to be limiting. The fastener form 2802 may include a single protrusion or multiple protrusions and the locking portion 2716 may include a single slot, a single hole, multiple slots, and/or multiple holes.

The term "a" or "an" means "at least one" or "one or more." The term "about" or "approximately" refers to a range of values within plus or minus 10% of the specified number. The term "substantially" means that the actual value is within about 10% of the actual desired value, particularly within about 5% of the actual desired value and especially within about 1% of the actual desired value of any variable, element or limit set forth herein.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims is to be understood to incorporate one or more such elements, neither requiring nor excluding two or more such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

The invention claimed is:

1. A system, comprising:
a leg calf shell further comprising a leg calf shell plantar flexion ridge at a lowermost point;
a boot shell rotatably connected to a bottom portion of the leg calf shell, wherein the boot shell comprises a boot shell plantar flexion ridge at an upper portion of the boot shell, wherein the boot shell plantar flexion ridge contacts the leg calf shell plantar flexion ridge at a plantar flexion ridges region and rotates no further; and
a strap configured to connect a side of the leg calf shell to the boot shell, wherein the strap comprises:
a first ring;
a first connector attached to a bottom portion of the first ring;
a second ring;
a second connector connected to a bottom portion of the second ring;
a non-stretch cord configured in a loop with a first portion of the loop connecting to the first connector and a second portion of the loop connecting to the second connector;
a hollow sheath positioned on a portion of the strap to be coaxial to the portion of the strap;
a first cover attached to the first connector and a first end of the hollow sheath to cover a first end of the hollow sheath and at least a portion of the first connector; and
a second cover attached to the second connector and a second end of the hollow sheath to cover a second end of the hollow sheath and at least a portion of the second connector.

2. The system of claim 1, further comprising a c-clip configured to fit over the hollow sheath, the first cover, or the second cover, wherein the c-clip is adapted to provide additional strength and structural integrity to the strap.

3. The system of claim 1, wherein:
the first ring is configured to connect to a back portion of the leg calf shell; and
the second ring is configured to connect to a back portion of the boot shell.

4. A device, comprising:
a leg calf shell further comprising a leg calf shell plantar flexion ridge at a lower portion;
a boot shell rotatably connected to a bottom portion of the leg calf shell, wherein the boot shell comprises a boot shell plantar flexion ridge at an upper portion of the boot shell, wherein the boot shell plantar flexion ridge contacts the leg calf shell plantar flexion ridge at a plantar flexion ridges region; and
a strap configured to connect a side of the leg calf shell to the boot shell, wherein the strap comprises:
a first buckle;
a first connector attached to a bottom portion of the first buckle;
a second buckle;
a second connector connected to a bottom portion of the second buckle;
a cord configured in a loop with a first portion of the loop connecting to the first connector and a second portion of the loop connecting to the second connector;
a hollow sheath positioned coaxial to the cord;
a first cover attached to the first connector and a first end of the hollow sheath to cover a first end of the hollow sheath and at least a portion of the first connector; and
a second cover attached to the second connector and a second end of the hollow sheath to cover a second end of the hollow sheath and at least a portion of the second connector.

5. An apparatus, comprising:
a first fastener;
a first connector attached to a bottom portion of the first fastener;
a second fastener;
a second connector connected to a bottom portion of the second fastener;
a cord configured in a loop with a first portion of the loop connecting to the first connector and a second portion of the loop connecting to the second connector;
a hollow sheath positioned coaxial to the cord;
a first cover attached to the first connector and a first end of the hollow sheath to cover a first end of the hollow sheath and at least a portion of the first connector; and
a second cover attached to the second connector and a second end of the hollow sheath to cover a second end of the hollow sheath and at least a portion of the second connector.

6. The apparatus of claim 5, wherein:
the first fastener is at least one of a first buckle, a first loop, a first ring, a first clasp, or a first clip; and
the second fastener is at least one of a second buckle, a second loop, a second ring, a second clasp, or a second clip.

* * * * *